US011203739B2

(12) United States Patent
Finley et al.

(10) Patent No.: US 11,203,739 B2
(45) Date of Patent: Dec. 21, 2021

(54) MODULATING CELL PROLIFERATION AND PLURIPOTENCY

(71) Applicants: Memorial Sloan Kettering Cancer Center, New York, NY (US); The Rockefeller University, New York, NY (US)

(72) Inventors: Lydia W. S. Finley, New York, NY (US); Bryce W. Carey, New York, NY (US); Craig B. Thompson, New York, NY (US); C. David Allis, New York, NY (US)

(73) Assignees: Memorial Sloan-Kettering Cancer Center, New York, NY (US); The Rockefeller University, New York, NY (US)

(*) Notice: Subject to any disclaimer, the term of this patent is extended or adjusted under 35 U.S.C. 154(b) by 3 days.

(21) Appl. No.: 15/302,560

(22) PCT Filed: Apr. 7, 2015

(86) PCT No.: PCT/US2015/024749
§ 371 (c)(1),
(2) Date: Oct. 7, 2016

(87) PCT Pub. No.: WO2015/157310
PCT Pub. Date: Oct. 15, 2015

(65) Prior Publication Data
US 2017/0022475 A1 Jan. 26, 2017

Related U.S. Application Data

(60) Provisional application No. 62/066,294, filed on Oct. 20, 2014, provisional application No. 61/976,488, filed on Apr. 7, 2014.

(51) Int. Cl.
*C12N 5/0735* (2010.01)
*C12N 5/074* (2010.01)
*A61K 31/194* (2006.01)

(52) U.S. Cl.
CPC .......... *C12N 5/0606* (2013.01); *A61K 31/194* (2013.01); *C12N 5/0696* (2013.01); *C12N 2500/30* (2013.01); *C12N 2501/727* (2013.01)

(58) Field of Classification Search
CPC ................ C12N 5/0606; C12N 5/0696; C12N 2500/30; C12N 2501/727; A61K 31/194
See application file for complete search history.

(56) References Cited

U.S. PATENT DOCUMENTS 5,942,435 A    8/1999  Wheeler
2008/0254513 A1* 10/2008  Cayli .................... C12N 5/0018
                                                    435/70.1
2010/0317100 A1* 12/2010  Paul ..................... C07D 403/04
                                                    435/353
2011/0008302 A1   1/2011  Tsichlis et al.
2011/0110914 A1   5/2011  Narain et al.
2013/0236973 A1   9/2013  Rezania
2013/0302893 A1* 11/2013  Pei ....................... C12N 5/0662
                                                    435/377

FOREIGN PATENT DOCUMENTS

JP   2011-511935 A      4/2011
WO   WO-2008/085879 A2  7/2008
WO   WO-2010/077955 A1  7/2010
WO   WO-2011/140397 A2  11/2011
WO   WO-2011140397 A2 * 11/2011 ........... C12N 5/0606

OTHER PUBLICATIONS

Xiao et al Genes Dev. vol. 26. No. 12, 1326-1338 (Year: 2012).*
Ying et al Nature 453, 22, 519-524 (Year: 2008).*
Sato et al Nature Medicine, 10, 55-63 (Year: 2004).*
Brevini et al., Theriogenology, vol. 74, pp. 544-550 (Year: 2010).*
Paris et al. , Theriogenology, vol. 74, pp. 516-524 (Year: 2010).*
Munoz et al. Theriogenology, vol. 69, 1159-1164 (Year: 2008).*
Meng et al Cell Research 23:658-672 (Year: 2013).*
Xiao et al Genes & Dev. 26: 1326-1338 (Year: 2012).*
Wise et al Proc Natl Acad Sci U S A. 6;108(49):19611-6 a (Year: 2011).*
Lunt et al Annu. Rev. Cell Dev. Biol. 27:441-64 (Year: 2011).*
Carey, B. et al., Intracellular α-ketoglutarate maintains the pluripotency of embryonic stem cells, Nature, 518(7539):413-416 (2015).
International Search Report for PCT/US15/24749, 5 pages (dated Oct. 15, 2015).
Mackenzie, E. et al., Cell-Permeating α-Ketoglutarate Derivatives Alleviate Pseudohypoxia in Succinate Dehydrogenase-Deficient Cells, Molecular and Cellular Biology, 27(9):3282-3289 (2007).
Wise, D. et al., Hypoxia promotes isocitrate dehydrogenase-dependent carboxylation of ∞-ketoglutarate to citrate to support cell growth and viability, PNAS, 108(49):19611-19616 (2011).
Written Opinion for PCT/US15/24749, 15 pages (dated Oct. 15, 2015).
Xiao, M. et al., Inhibition of ∞-KG-dependent histone and DNA demethylases by fumarate and succinate that are accumulated in mutations of FH and SDH tumor suppressors, Genes & Development, 26:1326-1338 (2012).
Gafni, O. et al., Derivation of novel human ground state naive pluripotent stem cells, Nature, 504(7479):282-6 (2013).
Hanna, J. et al., Human embryonic stem cells with biological and epigenetic characteristics similar to those of mouse ESCs, Proc Natl Acad Sci USA, 107(20):9222-9227 (2010).
Diabetes, 60(1):p. A536, Abstract No. 1990-P, EMBASE (online), retrieved on Mar. 18, 2019, EMBASE Accession No. 0050623024 (2011).

(Continued)

*Primary Examiner* — Anoop K Singh
(74) *Attorney, Agent, or Firm* — Wolf, Greenfield & Sacks, P.C.

(57) ABSTRACT

Disclosed herein are compositions, systems, and methods for modulating proliferation, differentiation and pluripotency of cells.

6 Claims, 16 Drawing Sheets
Specification includes a Sequence Listing.

(56) References Cited

OTHER PUBLICATIONS

Habibi, E. et al., Whole-Genome Bisulfite Sequencing of Two Distinct Interconvertible DNA Methylomes of Mouse Embryonic Stem Cells, Cell Stem Cell, 13:360-369 (2013).

Panten, U. and Rustenbeck, I., Fuel-induced amplication of insulin secretion in mouse pancreatic islets exposed to a high sulfonylurea concentration: role of the NADPH/NADP$^+$ ratio, Diabetologia, 51:101-109 (2008).

Willenborg, M. et al., Triggering and amplification of insulin secretion by dimethyl α-ketoglutarate, a membrane permeable α-ketoglutarate analoge, European Journal of Pharmacology, 607:41-46 (2009).

* cited by examiner

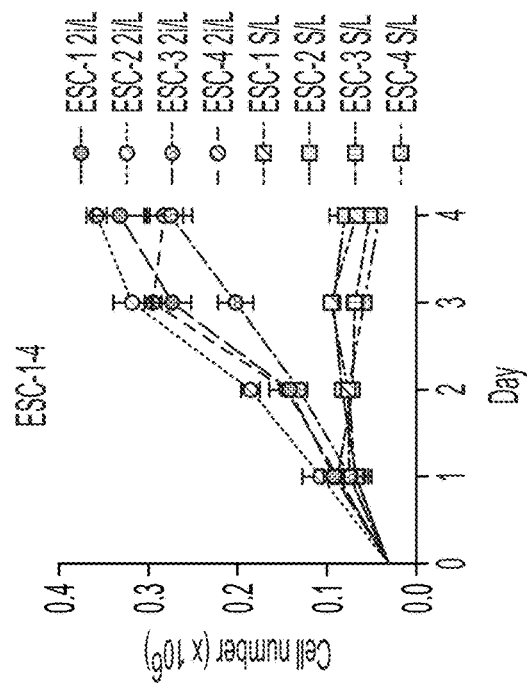
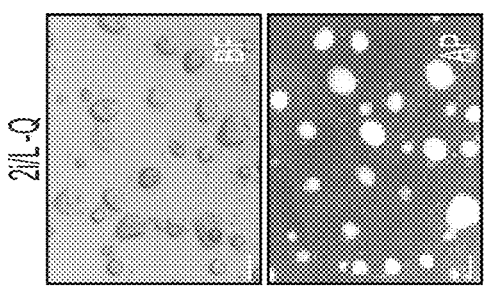
FIG. 1B
FIG. 1C
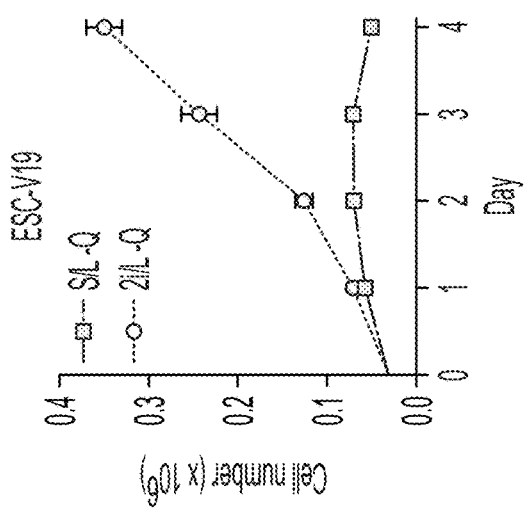
FIG. 1A

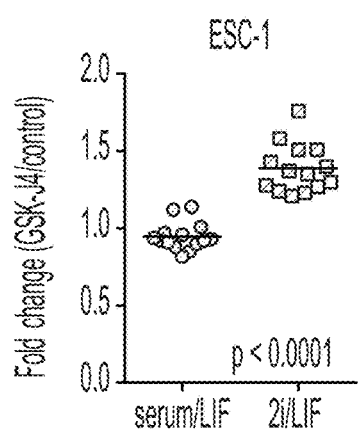
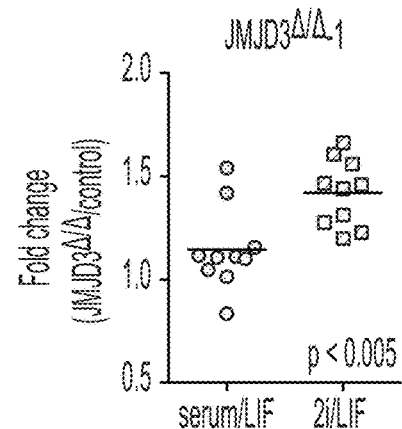
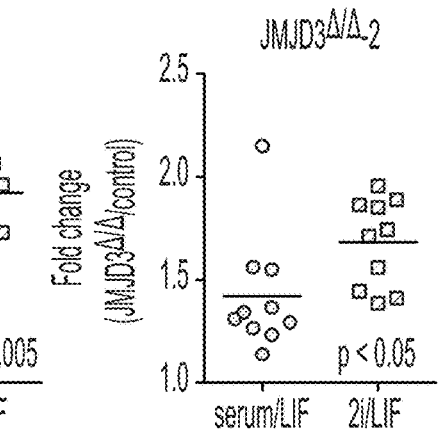
FIG. 3E
FIG. 3F
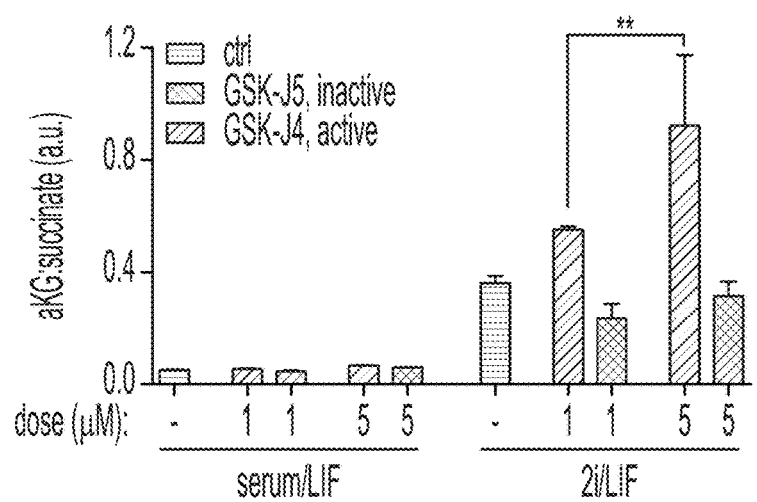
FIG. 3G

S/L+DMSO     S/L+DM-succinate     S/L+DM-αKG

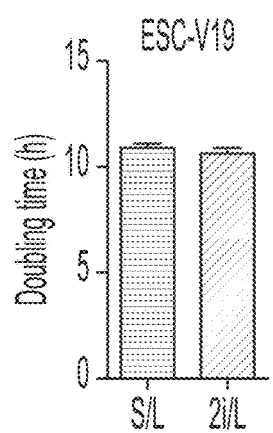
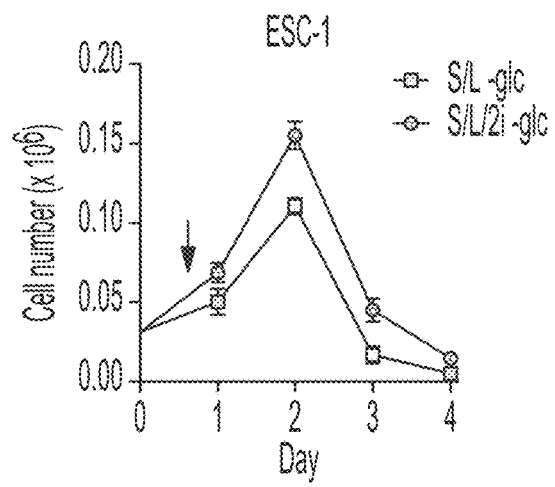
FIG. 5A  FIG. 5B
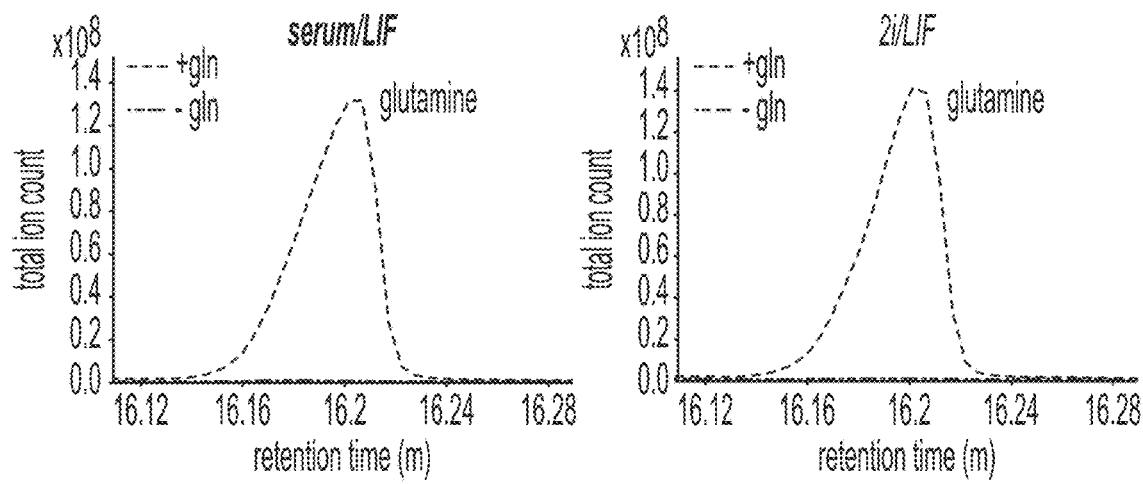
FIG. 5C
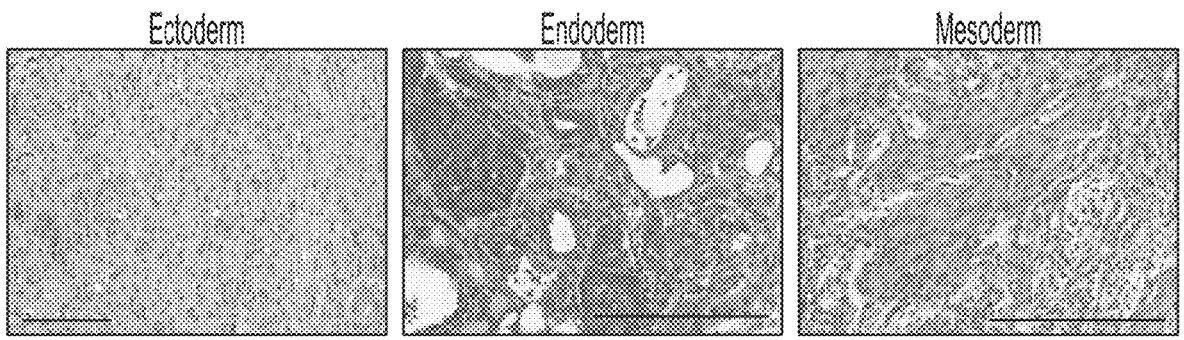
FIG. 5D

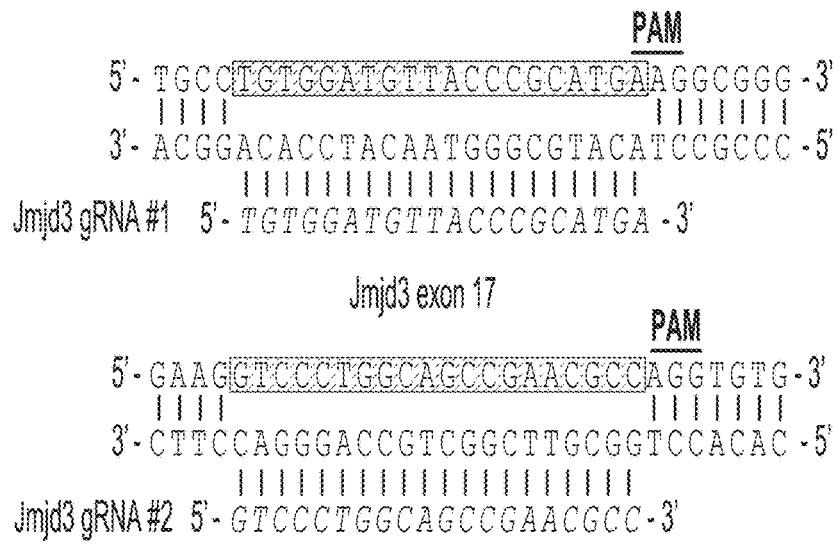
FIG. 8A
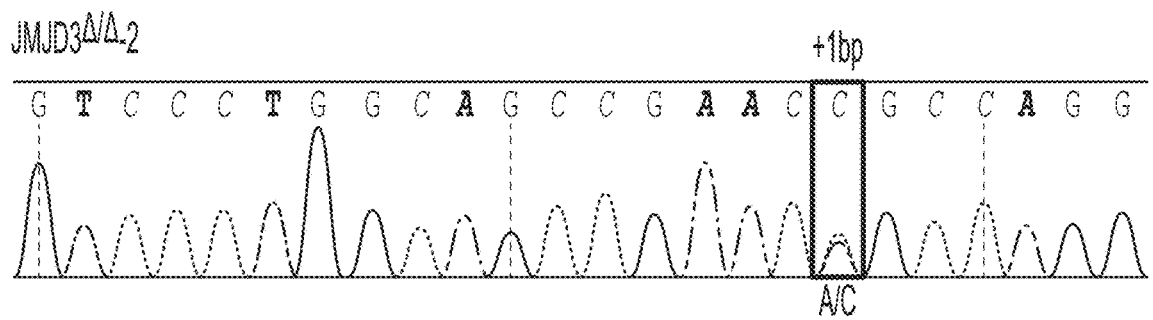
FIG. 8B
FIG. 8C

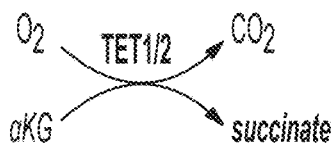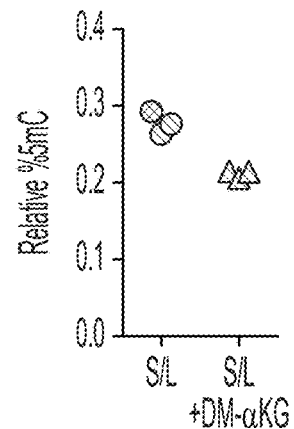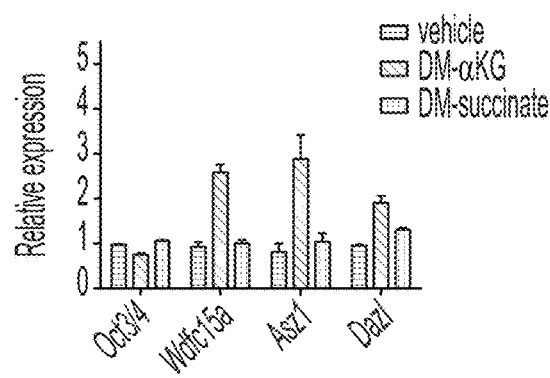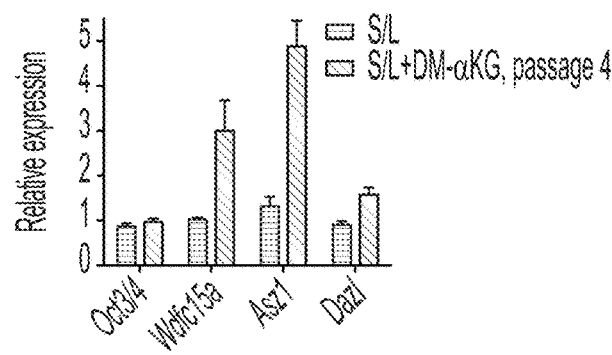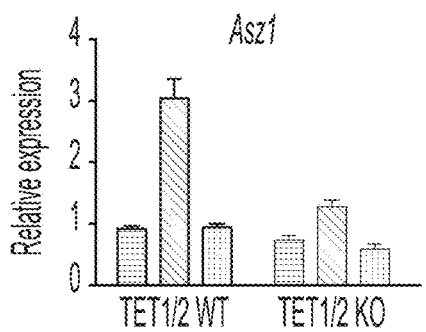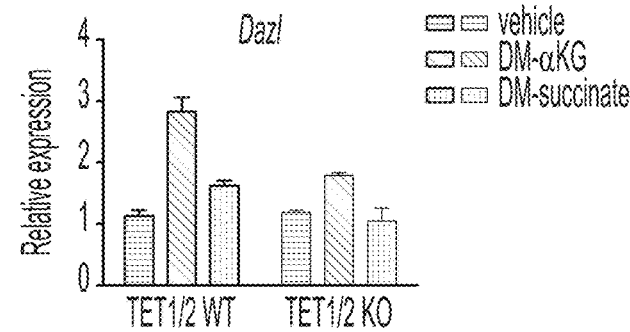
FIG. 9A
FIG. 9B
FIG. 9C
FIG. 9D
FIG. 9E

MODULATING CELL PROLIFERATION AND PLURIPOTENCY

RELATED APPLICATIONS

The present patent application is a national stage filing under 35 U.S.C. 371 of International Patent Application Ser. No. PCT/US2015/024749, filed Apr. 7, 2015, which claims the benefit of and priority to U.S. Provisional Patent Application Ser. No. 61/976,488, filed Apr. 7, 2014, and U.S. Provisional Patent Application Ser. No. 62/066,294, filed Oct. 20, 2014, which are hereby incorporated by reference in their entirety for any and all purposes.

GOVERNMENT SUPPORT

This invention was made with government support under CA008748 and CA105463 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 6, 2015, is named 2003080-0824_SL.txt and is 16,587 bytes in size.

BACKGROUND

Glutamine is a major metabolic substrate that contributes to macromolecular synthesis and tricarboxylic acid (TCA) cycle anaplerosis, among other cellular pathways. Most mammalian cells cannot proliferate without exogenous glutamine supplementation even though glutamine is a non-essential amino acid.

SUMMARY

The present invention encompasses the discovery that stem cell proliferation, differentiation and pluripotency can be controlled by manipulating cell metabolism. The present invention further comprises the discovery that intracellular α-ketoglutarate and/or succinate levels can be modulated to control cell self-renewal and differentiation.

In some embodiments, the invention provides compositions, methods, and systems for expanding a population of cells. In some embodiments, the methods comprise expanding cells in a cell culture. In some embodiments, methods comprise expanding cells ex vivo.

In some embodiments, the invention provides compositions, methods, and systems for maintaining cell pluripotency in a population of cells. In some embodiments, the cells are stems cells. In some embodiments, the cells are progenitor cells. In some embodiments, the cells are embryonic stems cells. In some embodiments, the cells are adult stems cells. In some embodiments, the cells are induced pluripotent stem cells (iPSC).

In some embodiments, the methods comprise steps of providing a cell culture comprising mammalian stem cells in a medium and maintaining α-ketoglutarate relative to succinate levels in the cells to facilitate proliferation or to maintain cell pluripotency. In some embodiments, the methods comprise steps of providing a cell culture comprising mammalian stem cells in a medium and maintaining α-ketoglutarate relative to succinate levels in the cells to maintain pluripotency.

In some embodiments, the methods comprise administering an agent or compound that increases α-ketoglutarate relative to succinate levels in the cells. In some embodiments, the methods comprise achieving or maintaining α-ketoglutarate in the cells at a level at least 20%, at least 30%, at least 40%, or at least 50% higher than that observed with cells maintained comparable conditions absent the agent or compound. In some embodiments, the invention provides compositions, systems, and methods for achieving or maintaining succinate in the cells at a level at least 20%, at least 30%, at least 40%, at least 50%, at least 60%, at least 70%, or at least 80% lower than that observed with cells maintained under comparable conditions absent the agent or compound.

In some embodiments, the invention provides compositions, systems, and methods for achieving or maintaining the ratio of α-ketoglutarate relative to succinate in the cells at a level at least 30%, at least 40%, at least 50%, at least 60%, at least 70%, at least 80%, at least 90%, at least 100%, at least 150%, or at least 250% higher than that observed with cells maintained comparable conditions absent the agent or compound.

In some embodiments, the invention provides compositions, systems and methods for regulating proliferation in a population of cells. In some embodiments, the invention provides compositions, systems, and methods for expanding stem cells or progenitor cells in a cell culture.

In some embodiments, the invention provides compositions, systems, and methods for regulating differentiation in a population of cells. In some embodiments, the invention provides compositions, systems, and methods for regulating differentiation in a cell culture.

In some embodiments, the invention provides compositions, systems, and methods for regulating proliferation or differentiation in a population of cells by maintaining α-ketoglutarate to succinate levels in the cells. In some embodiments, the invention provides compositions, systems, and methods for regulating proliferation or differentiation in a population of cells by administering an agent or compound that decreases α-ketoglutarate relative to succinate levels in the cells. In some embodiments, the invention provides compositions, systems, and methods for regulating proliferation or differentiation in a population of cells by contacting the cells with an exogenous succinate compound. In some embodiments, the exogenous succinate compound is cell permeable. In some embodiments, the succinate compound is dimethyl succinate (DM-succinate).

In some embodiments, the invention provides compositions, systems, and methods for regulating proliferation or differentiation in a population of cells by achieving or maintaining succinate in the cells at a level at least 20%, at least 30%, at least 40%, at least 50%, at least 50%, at least 60%, at least 70%, or at least 80% higher than that observed with cells maintained under comparable conditions absent the agent or compound. In some embodiments, the invention provides compositions, systems, and methods for regulating proliferation or differentiation in a population of cells by maintaining α-ketoglutarate in the cells at a level at least 20%, at least 30%, at least 40%, or at least 50% lower than that observed with cells maintained under comparable conditions absent the agent or compound. In some embodiments, the invention provides compositions, systems, and methods for regulating proliferation or differentiation in a population of cells by maintaining the ratio of α-ketoglutarate to succinate levels in the cells at least 30%, at least 40%, at least 50%, at least 60%, at least 70%, at least 80%, or at least 90% lower than that observed with cells maintained under comparable conditions absent the agent or compound.

In some embodiments, the invention provides compositions, systems, and methods for inhibiting proliferation of cells comprising administering an agent that decreases cellular levels of α-ketoglutarate. In some embodiments, the invention provides compositions, systems, and methods for inhibiting proliferation of cells comprising administering an agent that increases cellular levels of succinate. In some embodiments, the methods further comprise administering a MAPK inhibitor and/or a GSK3β inhibitor.

In some embodiments, the invention provides compositions, systems, and methods for inhibiting proliferation of cells for use in vivo. In some embodiments, the invention provides compositions, systems, and methods for inhibiting proliferation of cells for use ex vivo. In some embodiments, the invention provides compositions, systems, and methods for inhibiting proliferation of cells for use in vitro.

In some embodiments, the invention provides a cell culture comprising a population of stem cells or progenitor cells and a medium. In some embodiments, the medium comprises an α-ketoglutarate compound, a MAPK inhibitor, and/or a GSK3β inhibitor.

In some embodiments, the invention provides a substrate for cell culture. In some embodiments, the substrate comprises an α-ketoglutarate compound, a MAPK inhibitor, and/or a GSK3β inhibitor.

In some embodiments, the invention provides compositions, systems, and methods for promoting histone methylation in a cell. In some embodiments, the methods comprise contacting the cell with an agent that increases cellular α-ketoglutarate relative to succinate levels in the cell. In some embodiments, the methods comprise contacting the cell with an agent that decreases cellular α-ketoglutarate relative to succinate levels in the cell.

In some embodiments, the invention provides compositions, systems, and methods for inhibiting proliferation of cells in vivo. In some embodiments, the invention provides compositions, systems, and methods for inhibiting proliferation of cells in vivo in an animal. In some embodiments, the animal is a mammal. In some embodiments, the animal is a human. In some embodiments, invention provides administering to a subject in need thereof a therapeutic regimen. In some embodiments, the regimen comprises one or more doses of a succinate compound, one or more doses of an agent that increases cellular succinate, one or more doses of an agent that decreases cellular α-ketoglutarate, one or more doses of a glutamine synthase inhibitor, or combinations thereof.

In some embodiments, the invention provides compositions, systems, and methods for promoting differentiation of cells in vivo. In some embodiments, the invention provides compositions, systems, and methods for inhibiting proliferation of cells in vivo in an animal. In some embodiments, the animal is a mammal. In some embodiments, the animal is a human. In some embodiments, the methods comprise administering to a subject in need thereof a therapeutic regimen that comprises administration of one or more doses of a succinate compound, one or more doses of an agent that increases cellular succinate, one or more doses of an agent that decreases cellular α-ketoglutarate, one or more doses of a glutamine synthase inhibitor, or combinations thereof. In some embodiments, the invention provides compositions and systems for achieving delivery of the agent or compound to the cells.

In some embodiments, the invention provides compositions, systems, and methods for promoting cell proliferation in vivo in an animal. In some embodiments, the animal is a mammal. In some embodiments, the animal is a human. In some embodiments, the methods comprise administering to a subject in need thereof a therapeutic regimen that comprises one or more doses of an agent that is an α-ketoglutarate compound or increases cellular α-ketoglutarate.

In some embodiments, the invention provides compositions, systems, and methods for restoring a population of cells in vivo. In some embodiments, the cells are hematopoietic stem cells. In some embodiments, the invention provides compositions, systems, and methods for restoring a population of cells in vivo in a patient in which cells are depleted. In some embodiments, the patient is receiving or has received chemotherapy.

In some embodiments, the invention provides compositions, systems, and methods for maintaining pluripotency of a stem cell or a progenitor cell in vivo in a subject. In some embodiments, the methods comprise administering to the subject a therapeutic regimen that comprises administration of one or more doses of an agent that is an α-ketoglutarate compound or increases cellular α-ketoglutarate.

In some embodiments, the invention provides compositions, systems, and methods for maintaining pluripotency of a stem cell or a progenitor cell during transfer, transportation or storage. In some embodiments, the methods comprise contacting the cell with a composition that comprises an α-ketoglutarate compound or an agent that increases cellular α-ketoglutarate.

In some embodiments, the invention provides compositions, systems, and methods for enriching a population of cells for pluripotent cells. In some embodiments, the method comprises contacting a mixed population of cells with an α-ketoglutarate compound or an agent that increases α-ketoglutarate relative to succinate levels in the cells. In some embodiments, no exogenous glutamine is added to the medium. In some embodiments, pluripotent cells can be selected from cells that are not pluripotent cells because the former has higher proliferation rate compared to the latter. In some embodiments, pluripotent cells can be selected from cells that are not pluripotent cells because the former has higher survival rate compared to the latter. In some embodiments, the invention provides compositions, systems, and methods for enriching pluripotent cells to at least 50%, 60%, 70%, 80%, 90%, 95%, or 99% of the total population of cells.

In some embodiments, the invention provides compositions, systems, and methods for enriching a population of cells for pluripotent cells. In some embodiments, the method comprises contacting a mixed population of cells with a medium that has significantly reduced levels of glutamine. In some embodiments, no exogenous glutamine is added to the medium. In some embodiments, the invention provides compositions, systems, and methods for enriching pluripotent cells to at least 50%, 60%, 70%, 80%, 90%, 95%, or 99% of the total population of cells. In some embodiments, the pluripotent cells are stem cells. In some embodiments, the pluripotent cells are progenitor cells. In some embodiments, the pluripotent cells are induced.

In some embodiments, the invention provides methods for identifying a population of pluripotent cells, the method comprising providing a population of cells in a culture, wherein the culture comprises a medium that is substantially free of glutamine; and identifying the pluripotent cells based on cell survival.

In some embodiments, the invention provides methods for selecting a population of pluripotent cells, the method comprising providing a population of cells in a culture, wherein the culture comprises a medium that is substantially free of glutamine; and selecting the surviving cells.

In some embodiments, the invention provides compositions, systems, and methods for modulating DNA methylation in a cell. In some embodiments, the invention provides methods comprising a step of contacting the cell with an α-ketoglutarate compound or an agent that increases cellular α-ketoglutarate relative to succinate levels in the cell.

BRIEF DESCRIPTION OF THE DRAWINGS

FIGS. 1A to 1G depict line graphs for growth curves and representative images of ESCs grown in the absence of glutamine. Growth curves of ESC-V19 cells (FIG. 1A) and V6.5 ESC lines (ESC-1-4) (FIG. 1B) cultured in glutamine-free S/L or 2i/L medium. FIG. 1C, Phase images showing ESC-1 cells cultured in glutamine-free 2i/L medium for 3 days. Top, brightfield (BF); bottom, alkaline phosphatase (AP) staining. Bar, 500 µm. FIG. 1D, Growth curve of ESC-V19 cells in glutamine-free S/L or S/L+2i medium. FIG. 1E, Phase images of ESC-1 cells cultured in glutamine-free S/L+2i medium for 3 days. FIG. 1F, Growth curve of ESC-V19 cells cultured in two serum-free media formulations containing N2 and B27 supplements, 2i/L and Bmp4/L. FIG. 1G, Intracellular glutamate levels 8 hours after addition of medium with or without glutamine. Q, glutamine. Data are presented as the mean±s.d. of triplicate wells from a representative experiment.

FIG. 2A, Analysis of glucose uptake (upper), glutamine uptake (center) and lactate secretion (lower). FIG. 2B, Intracellular levels of αKG, succinate, malate and aspartate. Bars, mean of n=4 (FIG. 2A) or n=3 (FIG. 2B) replicate wells ± s.d. from representative experiments. FIG. 2C, Schematic of the TCA cycle including entry points for glucose- and glutamine-derived carbons. Isotope tracing was performed for metabolites shown in bold. FIGS. 2D-2E, Fraction of each metabolite labeled by 13C derived from [U-13C]glutamine (13C-gln) (FIG. 2D) or derived from [U-13C]glucose (13C-glc) (FIG. 2E) over time (0-12 hours, h). Averages ± s.e.m. of three independent experiments are shown. FIGS. 2F-2G, Glutamine (FIG. 2F) and glucose (FIG. 2G) flux through αKG and malate pools. Averages±s.e.m. of flux calculated for three independent experiments (shown in FIGS. 2D, 2E) are shown. *, $p<0.05$; , $p<0.005$; *, $p<0.0005$. p values determined by unpaired two-tailed Student's t-tests.

FIGS. 3A to 3G show FIG. 3A, GC-MS analysis of the αKG:succinate ratio in four ES cells lines (ESC-1-4) grown in either S/L or 2i/L media. *, $p<0.0001$ as determined by 2-way ANOVA with Sidak's multiple comparisons post-test. FIG. 3B, Western blot of ESC-1 and ESC-2 cells grown in 2i/L medium with or without glutamine for three days. FIG. 3C, Simplified schematic of the reaction mechanism of αKG-dependent dioxygenases (Fe(II) not shown). UTX and Jmjd3 are H3K27me3 demethylases; GSK-J4 is a UTX/Jmjd3-specific inhibitor. FIG. 3D, Western blot of ESC-1 cells grown in S/L in the presence of increasing amounts of the Jmjd3/UTX inhibitor GSK-J4 for 24 hours. FIG. 3E, H3K27me3 ChIP-PCR of ESC-1 cells cultured in S/L or 2i/L containing 30 µM UTX/Jmjd3 inhibitor GSK-J4 for five hours. Values represent fold-change (GSK-J4/control) at individual bivalent domain genes (n=14). $p<0.0001$ as determined by unpaired Student's t-test. FIG. 3F, H3K27me3 ChIP-PCR of JMJD3Δ/Δ−1 (left) and JMJD3 Δ/Δ−2 (right) cells cultured in S/L or 2i/L. Values represent fold-change (JMJD3 Δ/Δ cells relative to control cells) at individual bivalent domain genes (n=10). p values determined by unpaired Student's t-test. FIG. 3G, The ratio of αKG to succinate in ESC-1 cells grown in S/L or 2i/L medium with 1 µM or 5 µM of GSK-J4 or GSK-J5 for three hours. , $p<0.001$ determined by 2-way ANOVA with Sidak's multiple comparisons post-test. Data are presented as the mean±s.d (FIG. 3A) or s.e.m. (FIG. 3G) of triplicate wells from a representative experiment.

FIG. 4B, Quantification of colonies. Data are presented as the mean±s.e.m. of triplicate wells from a representative experiment. DM-αKG has more undifferentiated colonies than vehicle or DM-succinate treated wells, ***, $p<0.0001$ as calculated by 2-way ANOVA with Tukey's multiple comparisons post-test (FIG. 4A, 4B, Colony formation assay using ESC-1 cells. Cells were plated at clonal density and media changed to experimental media containing either DM-αKG or DM-succinate on day 2 and then analyzed 4 days later by alkaline phosphatase staining and scored for number of differentiated, mixed and undifferentiated or undifferentiated colonies). FIG. 4C, Quantification of mean GFP intensity of Nanog-GFP cells treated for three days with or without DM-αKG. Data are presented as the mean±s.d. (FIG. 4B) or 95% confidence intervals (FIG. 4C) of triplicate wells from a representative experiment.

FIGS. 5A to 5L show FIG. 5A, a bar graph of doubling time of ESC-V19 cells cultured in serum/LIF (S/L) or 2i/LIF (2i/L). FIG. 5B, Growth curve of ESC-1 cells cultured in S/L or S/L+2i medium devoid of glucose. FIG. 5C, Samples of S/L (left) and 2i/L (right) media with and without glutamine were analyzed by gas chromatography-mass spectrometry. Representative chromatograms of the total ion count reveal a clear glutamine (Q) peak in +Q media (short dashes) and no detectable glutamine in −Q media (long dashes). m, minutes. FIG. 5D, Teratoma formation from ESCs grown in 2i/L medium without glutamine for three days. Representative images of haematoxylin and eosin staining reveal neural tissue (ectoderm), hepatocytes and pancreatic acinar cells (endoderm) and smooth muscle (mesoderm). Scale bar, 200 µm. FIG. 5E, Growth curve of ESC-1 cells grown in glutamine-free 2i/L or 2i medium. FIG. 5F, Gene expression analysis confirms that epiblast stem cells (EpiSCs) were generated from ESC-1 cells by culture with Fgf and Activin A. Transcript levels were assessed by qRT-PCR, normalized to Gapdh and expressed as a ratio of values of mESCs cultured in 2i/L medium. FIG. 5G, Growth curve of EpiSCs cultured in epiblast medium (Fgf/ActA) with or without glutamine. FIG. 5H, Growth curve of an induced pluripotent (iPS) cell line derived from fibroblasts using Oct3/4 (O), Klf4 (K), and Sox2 (S) cultured in glutamine-free S/L or 2i/L media. FIG. 5I, Doubling time of ESC-1 cells cultured in 2i/L medium in the presence and absence of glutamine. FIG. 5J, Growth curve ESC-V19 cells cultured in glutamine-free 2i/L media in the presence or absence of 1 µM methylsulfoxide (MSO). FIGS. 5K-5L, ESC-V19 cells grown in glutamine free S/L media (FIG. 5K) or 2i/L media (FIG. 5L) with or without 4 mM dimethyl-α-ketoglutarate (DM-αKG). For growth curve experiments, cells were seeded on day 0 in complete medium and then were changed to experimental medium on day 1. Data are presented as the mean±s.d of triplicate wells from a representative experiment.

FIG. 6B, 2i medium enables glutamate synthesis from glucose-derived carbons. ESC-1 cells were cultured in S/L, S/L/2i or 2i/L medium containing [U-$^{13}$C]glucose for four hours and the fraction of glutamate containing glucose-derived carbons is shown. Incorporation of $^{14}$C derived from [U-$^{14}$C]glutamine ($^{14}$C-gln) (FIG. 6C) or derived from [U-$^{14}$C]glucose ($^{14}$C-glc) (FIG. 6D) into total cellular protein after 48 hour incubations. $p<0.05$ for $^{14}$C-glc, $p=0.1$ for $^{14}$C-gln, calculated by unpaired two-tailed Student's t-test. Data are presented as the mean±s.d (FIG. 6A, 6B) or ±s.e.m (FIG. 6C) of triplicate wells from a representative.

FIGS. 7B-7C, H3K27me3 ChIP-PCR of ESC-1 cells cultured in S/L (FIG. 7B) or 2i/L (FIG. 7C) medium with or without 30 µM UTX/Jmjd3 inhibitor GSK-J4 for five hours. Data are presented as the mean±s.e.m. of triplicate samples from a representative experiment. *, $p<0.05$ by unpaired Student's two-tailed t-test.

FIGS. 8A to 8C show FIG. 8A, Schematic of targeting strategy for gRNAs to mouse Jmjd3 exon 17. gRNA sequences are highlighted in box. FIG. 8B, Representative sequences from two clones used in this study. Sanger sequencing revealed indels as shown in schematic. Dashes indicate deleted bases; Underlined bases, insertions. gRNA is highlighted with box and PAM sequences identified in as AGG. Predicted cut site indicated by dashed triangle. Location of in-frame downstream stop is indicated on the right. FIG. 8C, An example chromatogram for clone JMJD3 Δ/Δ−2 showing single base-pair insertions at predicted Cas9 cleavage site. Top to bottom, left to right, the sequences shown in FIGS. 8A to 8B include the following: 5'-TGC CTG TGG ATG TTA CCC GCA TGA AGG CGG G 3' (SEQ ID NO: 1); 3'-ACG GAC ACC TAC AAT GGG CGT ACA TCC GCC C 5' (SEQ ID NO: 2); 5'-TGT GGA TGT TAC CCG CAT GA-3'(SEQ ID NO: 3); 5'-GAA GGT CCC TGG CAG CCG AAC GCC AGG TGT G-3'(SEQ ID NO: 4); 3'-CTT CCA GGG ACC GTC GGC TTG CGG TCC ACA C-5'(SEQ ID NO: 5); 5'-GTC CCT GGC AGC CGA ACG CC-3'(SEQ ID NO: 6); 5' TGT GGA TGT TAC CCG CAT GAA GG 3'(SEQ ID NO: 7); 5' TGT GGA TGT TAC CCG TGA AGG 3'(SEQ ID NO: 8); 5' TGT GGA TGT TAC CCG AAG G 3'(SEQ ID NO: 9); 5' GTC CCT GGC AGC CGA ACG CCA GG 3'(SEQ ID NO: 10); 5' GTC CCT GGC AGC CGA ACA GCC AGG 3'(SEQ ID NO: 11); 5' GTC CCT GGC AGC CGA ACC GCC AGG 3'(SEQ ID NO: 12).

FIGS. 9A to 9E show FIG. 9A, A diagram of Tet 1/2's role in αKG to succinate conversion. FIG. 9B, Relative percent 5-methylcytosine (% 5mC) in ESC-1 cells cultured in S/L medium with or without DM-αKG for 24 hours. Each data point represents a sample from triplicate wells of a representative experiment. FIG. 9C, Gene expression in ESC-1 cells cultured with DM-αKG or DM-succinate for three days. FIG. 9D, ESC-1 cells were cultured in S/L medium with DM-αKG for 24 hours or four passages. FIG. 9E, Wild-type or Tet1/Tet2 double knock out (KO) mESCs were cultured with DM-αKG or DM-succinate for 72 hours. qRT-PCR data (FIGS. 9B-9D) was normalized to Actin or Gapdh and samples were normalized to the control group. Oct3/4 is not expected to change and is included as a control. Data are presented as the ±s.e.m. of triplicate wells from a representative experiment.

FIG. 10B, ESC-1 cells were cultured with DM-αKG for four passages and then switched to medium containing the indicated amounts of DM-αKG for three days. GFP expression (mean fluorescence intensity, M.F.I.) was determined by FACS. Bars±s.d. of triplicate wells from a representative.

DEFINITIONS

Figure 1D:
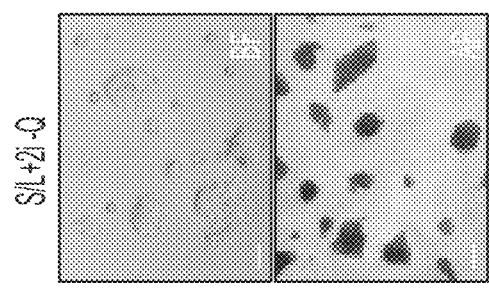

Unless otherwise indicated, the terms used herein have the person skilled in the art as commonly understood meaning, in order to facilitate understanding of the present disclosure, some terms will be used herein, the following definitions.

In order for the present invention to be more readily understood, certain terms are first defined below. Additional definitions for the following terms and other terms are set forth throughout the specification.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Activating agent: As used herein, the term "activating agent," or activator, refers to an agent whose presence or level correlates with elevated level or activity of a target, as compared with that observed absent the agent (or with the agent at a different level). In some embodiments, an activating agent is one whose presence or level correlates with a target level or activity that is comparable to or greater than a particular reference level or activity (e.g., that observed under appropriate reference conditions, such as presence of a known activating agent, e.g., a positive control).

Administration: As used herein, the term "administration" refers to the administration of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

Agent: The term "agent" as used herein may refer to a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form.

Amino acid: As used herein, term "amino acid," in its broadest sense, refers to any compound and/or substance that can be incorporated into a polypeptide chain. In some embodiments, an amino acid has the general structure H2N—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog a substance that can be generated from the reference substance by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Animal: As used herein, the term "animal" refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Antagonist: As used herein, the term "antagonist" refers to an agent that i) inhibits, decreases or reduces the effects of another agent, for example that inactivates a receptor; and/or ii) inhibits, decreases, reduces, or delays one or more biological events, for example, activation of one or more receptors or stimulation of one or more biological pathways. In particular embodiments, an antagonist inhibits activation and/or activity of one or more receptor tyrosine kinases. Antagonists may be or include agents of any chemical class including, for example, small molecules, polypeptides, nucleic acids, carbohydrates, lipids, metals, and/or any other entity that shows the relevant inhibitory activity. An antagonist may be direct (in which case it exerts its influence directly upon the receptor) or indirect (in which case it exerts its influence by other than binding to the receptor; e.g., altering expression or translation of the receptor; altering signal transduction pathways that are directly activated by the receptor, altering expression, translation or activity of an agonist of the receptor).

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Combination therapy: The term "combination therapy", as used herein, refers to those situations in which two or more different pharmaceutical agents for the treatment of disease are administered in overlapping regimens so that the subject is simultaneously exposed to at least two agents. In some embodiments, the different agents are administered simultaneously. In some embodiments, the administration of one agent overlaps the administration of at least one other agent. In some embodiments, the different agents are administered sequentially such that the agents have simultaneous biologically activity with in a subject.

Comparable: The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

Derivative: As used herein, the term "derivative" refers to a structural analogue of a reference substance. That is, a "derivative" is a substance that shows significant structural similarity with the reference substance, for example sharing a core or consensus structure, but also differs in certain discrete ways. In some embodiments, a derivative is a substance that can be generated from the reference substance by chemical manipulation. In some embodiments, a derivative is a substance that can be generated through performance of a synthetic process substantially similar to (e.g., sharing a plurality of steps with) one that generates the reference substance.

Determine: It is appreciated by those of skill in the art that "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Diagnostic information: As used herein, diagnostic information or information for use in diagnosis is any information that is useful in determining whether a patient has a disease or condition and/or in classifying the disease or condition into a phenotypic category or any category having significance with regard to prognosis of the disease or condition, or likely response to treatment (either treatment in general or any particular treatment) of the disease or condition. Similarly, diagnosis refers to providing any type of diagnostic information, including, but not limited to, whether a subject is likely to have a disease or condition (such as cancer), state, staging or characteristic of the disease or condition as manifested in the subject, information related to the nature or classification of a tumor, information related to prognosis and/or information useful in selecting an appropriate treatment. Selection of treatment may include the choice of a particular therapeutic (e.g., chemotherapeutic) agent or other treatment modality such as surgery, radiation, etc., a choice about whether to withhold or deliver therapy, a choice relating to dosing regimen (e.g., frequency or level of one or more doses of a particular therapeutic agent or combination of therapeutic agents), etc.

Dosage form: As used herein, the terms "dosage form" and "unit dosage form" refer to a physically discrete unit of a therapeutic composition to be administered to a subject. Each unit contains a predetermined quantity of active material (e.g., a therapeutic agent such as an anti-receptor tyrosine kinases antibody). In some embodiments, the predetermined quantity is one that has been correlated with a desired therapeutic effect when administered as a dose in a dosing regimen. Those of ordinary skill in the art appreciate that the total amount of a therapeutic composition or agent administered to a particular subject is determined by one or more attending physicians and may involve administration of multiple dosage forms.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, a dosing regimen is or has been correlated with a desired therapeutic outcome, when administered across a population of patients.

Functional: As used herein, a "functional" biological molecule is a biological molecule in a form in which it exhibits a property and/or activity by which it is characterized. A biological molecule may have two functions (i.e., bifunctional) or many functions (i.e., multifunctional).

Isomer: As is known in the art, many chemical entities (in particular many organic molecules and/or many small molecules) can exist in a variety of structural and/or optical isomeric forms. In some embodiments, as will be clear to those skilled in the art from context, depiction of or reference to a particular compound structure herein is intended to encompass all structural and/or optical isomers thereof. In some embodiments, as will be clear to those skilled in the art from context, depiction of or reference to a particular compound structure herein is intended to encompass only the depicted or referenced isomeric form. In some embodiments, compositions including a chemical entity that can exist in a variety of isomeric forms include a plurality of such forms; in some embodiments such compositions include only a single form. For example, in some embodiments, compositions including a chemical entity that can exist as a variety of optical isomers (e.g., stereoisomers, diastereomers, etc) include a racemic population of such optical isomers; in some embodiments such compositions include only a single optical isomer and/or include a plurality of optical isomers that together retain optical activity.

Marker: A marker, as used herein, refers to an agent whose presence or level is a characteristic of a particular tumor or metastatic disease thereof. For example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy.

Mass spectrometry: Mass spectrometry refers to method using a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these.

Metabolite: As used herein, "metabolite" refers to any substance produced or used during a physical or chemical process within the body that creates or uses energy, such as: digesting food and nutrients, eliminating waste through urine and feces, breathing, circulating blood, and regulating temperature. The term "metabolic precursors" refers to compounds from which the metabolites are made. The term "metabolic products" refers to any substance that is part of a metabolic pathway (e.g., metabolite, metabolic precursor).

Modulator: The term "modulator" is used to refer to an entity whose presence in a system in which an activity of interest is observed correlates with a change in level and/or nature of that activity as compared with that observed under otherwise comparable conditions when the modulator is absent. In some embodiments, a modulator is an activator, in that activity is increased in its presence as compared with that observed under otherwise comparable conditions when the modulator is absent. In some embodiments, a modulator is an inhibitor, in that activity is reduced in its presence as compared with otherwise comparable conditions when the modulator is absent. In some embodiments, a modulator interacts directly with a target entity whose activity is of interest. In some embodiments, a modulator interacts indirectly (i.e., directly with an intermediate agent that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pluripotency: As used herein, the term "pluripotency" "pluripotent" or "pluripotent state" refers to the properties of a cell, i.e., an ability to differentiate into a variety of tissues or organs. For example, in some embodiments, a pluripotent cell is a cell with the ability to differentiate into all three embryonic germ layers: endoderm (e.g., gut tissue), mesoderm (e.g., blood, muscle, and vessels), and ectoderm (e.g., skin and nerve). Pluripotent cells typically have the potential to divide extensively.

Progenitor cell: As used herein, the term "progenitor cell" refers to cells that have greater developmental potential, i.e., a cellular phenotype that is more primitive (e.g., is at an earlier step along a developmental pathway or progression) relative to a cell which it can give rise to by differentiation. Often, progenitor cells have significant or very high proliferative potential. Progenitor cells can give rise to multiple distinct cells having lower developmental potential, i.e., differentiated cell types, or to a single differentiated cell type, depending on the developmental pathway and on the environment in which the cells develop and differentiate.

Prognostic and predictive information: As used herein, the terms prognostic and predictive information are used interchangeably to refer to any information that may be used to indicate any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Reference: The term "reference" is often used herein to describe a standard or control agent or value against which an agent or value of interest is compared. In some embodiments, a reference agent is tested and/or a reference value is determined substantially simultaneously with the testing or determination of the agent or value of interest. In some embodiments, a reference agent or value is a historical reference, optionally embodied in a tangible medium. Typically, as would be understood by those skilled in the art, a reference agent or value is determined or characterized under conditions comparable to those utilized to determine or characterize the agent or value of interest.

Risk: As will be understood from context, a "risk" of a disease, disorder or condition is a degree of likelihood that a particular individual will develop the disease, disorder, or condition. In some embodiments, risk is expressed as a percentage. In some embodiments, risk is from 0, 1, 2, 3, 4, 5, 6, 7, 8, 9, 10 up to 100%. In some embodiments risk is expressed as a risk relative to a risk associated with a reference sample or group of reference samples. In some embodiments, a reference sample or group of reference samples have a known risk of a disease, disorder, or condition. In some embodiments a reference sample or group of reference samples are from individuals comparable to a particular individual. In some embodiments, relative risk is 0, 1, 2, 3, 4, 5, 6, 7, 8, 9, 10 or more.

Sample: As used herein, a sample obtained from a subject may include, but is not limited to, any or all of the following: a cell or cells, a portion of tissue, blood, serum, ascites, urine, saliva, and other body fluids, secretions, or excretions. The term "sample" also includes any material derived by processing such a sample. Derived samples may include nucleotide molecules or polypeptides extracted from the sample or obtained by subjecting the sample to techniques such as amplification or reverse transcription of mRNA, etc.

Small molecule: As used herein, the term "small molecule" means a low molecular weight organic and/or inorganic compound. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is a modulating agent. In some embodiments, a small molecule is biologically active. In some embodiments, a small molecule is detectable (e.g., comprises at least one detectable moiety). In some embodiments, a small molecule is a therapeutic.

Specific: The term "specific", when used herein with reference to an agent or entity having an activity, is understood by those skilled in the art to mean that the agent or entity discriminates between potential targets or states. For example, an agent is said to bind "specifically" to its target if it binds preferentially with that target in the presence of competing alternative targets. In some embodiments, the agent or entity does not detectably bind to the competing alternative target under conditions of binding to its target. In some embodiments, the agent or entity binds with higher on-rate, lower off-rate, increased affinity, decreased dissociation, and/or increased stability to its target as compared with the competing alternative target(s).

Stem cells: The term "stem cells" include but are not limited to undifferentiated cells defined by their ability at the single cell level to both self-renew and differentiate to produce progeny cells, including self-renewing progenitors, non-renewing progenitors, and terminally differentiated cells. For example, "stem cells" may include (1) totipotent stem cells; (2) pluripotent stem cells; (3) multipotent stem cells; (4) oligopotent stem cells; and (5) unipotent stem cells. Stem cells may originate from embryonic or adult sources. Stem cells that can be used for the purposes of the present invention include, without limitation, embryonic stem cells or reprogrammed stem cells, e.g., induced pluripotent stem cells, or cells obtained from somatic cell nuclear transfer (SCNT).

Subject: By "subject" is meant a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. A subject can be a patient, which refers to a human presenting to a medical provider for diagnosis or treatment of a disease. In some embodiments, a subject is an individual to whom therapy is administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition has been diagnosed with and/or exhibits or has exhibited one or more symptoms or characteristics of the disease, disorder, or condition.

Susceptible to: An individual who is "susceptible to" a disease, disorder, or condition is at risk for developing the disease, disorder, or condition. In some embodiments, such an individual is known to have one or more susceptibility factors that are statistically correlated with increased risk of development of the relevant disease, disorder, and/or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from allergy, etc.

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom. For example, many cancer patients with smaller tumors have no symptoms. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutic agent: As used herein, the phrase "therapeutic agent" refers to any agent that has a therapeutic effect and/or elicits a desired biological and/or pharmacological effect, when administered to a subject.

Therapeutically effective amount: As used herein, the term "therapeutically effective amount" refers to an amount of a therapeutic protein which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition (e.g., cancer). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Unit dose: The expression "unit dose" as used herein refers to an amount administered as a single dose or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components alternatively or additionally to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs or additional therapies used in combination or coincidental with specific compound(s) employed, and like factors well known in the medical arts.

DETAILED DESCRIPTION OF CERTAIN EMBODIMENTS

The invention encompasses the discovery that stem cell proliferation and pluripotency can be controlled by manipulating cell metabolism. The invention further comprises the discovery that intracellular α-ketoglutarate:succinate levels can be modulated to control cell self-renewal and differentiation.

Cell Fate Determination Using a Model of Embryonic Stem Cells

Stem cells such as embryonic stem cells (ESCs) grown under conditions that maintain pluripotency are capable of proliferation in the absence of exogenous glutamine, demonstrating that they are capable of synthesizing glutamine from glucose-derived α-ketoglutarate (αKG). Despite this, ESCs consume high levels of glutamine when the metabolite is available. Using isotope tracing studies, the inventors find that in comparison to differentiated cells, naïve ESC direct the glutamine they acquire away from consumption in the TCA cycle and protein synthesis and instead utilize glutamine to maintain a pool of αKG that promotes histone demethylation and sustains pluripotency. Naïve ESCs exhibit a significant increase in the ratio of αKG to succinate sufficient to alter the equilibrium balance of αKG-dependent reactions. Additionally, the inventors demonstrate that relative levels of αKG:succinate can regulate multiple histone modifications associated with both constitutive and facultative heterochromatin, including H3K27me3 at "bivalent domain" genes important for lineage determination during development[1,2]. This work reveals intracellular αKG:succinate levels can contribute to the maintenance of cellular identity and play a mechanistic role in the transcriptional and epigenetic state of naïve pluripotent cells.

One can determine the fate of a cell or population of cells following culture methods of the present invention to modulate intracellular relative αKG:succinate levels.

In some embodiments, cell fate is ascertained by one or more methods in the art that identify genotype, phenotype, morphology, gene expression, metabolic markers, cell surface markers, and/or cellular functional assay of the cell. In some embodiments, gene expression of one or more particular genes is identified following exposure of the cells to particular conditions, such as culturing in a particular medium. Gene level, protein level, and/or function may be ascertained, for example using Northern blot, Western blot, Southern blot, flow cytometry, ELISA, qPCR, and so forth. In some embodiments, cell maturity is determined by epigenetic changes, e.g., histone modification patterns. In specific embodiments, the genes encode proteins that are involved in a particular pathway associated with aerobic respiration and its associated pathways, including oxidative phosphorylation, the citric acid cycle (TCA), fatty acid oxidation, pyruvate decarboxylation, and the like. In specific embodiments, the genes may include CPT1 or PPARa (genes associated with fatty acid oxidation). In some cases, the genes encode proteins that signify development of a mature type of cell, such as hormone expression (such as decreased expression of NPPA/ANP and NPPB/BNP) and structural proteins associated with maturation (such as gain of myosin light chain 2V expression but loss of smooth muscle actin and skeletal actin expression).

Controlling Cell Fate in Cell Culture

The present invention also provides compositions, systems, and methods for maintaining pluripotency and/or self-renewing characteristics, or those for promoting cell differentiation, of a stem cell or a progenitor cell via manipulating cellular αKG:succinate levels in a cell culture.

Described herein is the surprising finding that controlling αKG:succinate levels significantly improves the maintenance and/or induction of pluripotency in cells. Combination of an αKG compound or an αKG activator with a MAPK inhibitor (e.g., a MEK inhibitor, an Erk inhibitor or a p38 inhibitor) or a GSK3β inhibitor allows for induction and/or maintenance of pluripotency of cells.

In some embodiments, the invention provides compositions, systems, and methods for culturing cells. In some embodiments, methods comprise steps of providing a cell culture comprising mammalian stem cells in a medium and maintaining α-ketoglutarate relative to succinate levels in the cells to facilitate proliferation. In some embodiments, methods comprise steps of providing a cell culture comprising mammalian stem cells in a medium and achieving or maintaining α-ketoglutarate relative to succinate levels in the cells to maintain pluripotency. In some embodiments, the cells are contacted with an exogenous α-ketoglutarate compound. In some embodiments, an exogenous α-ketoglutarate compound is added to the medium. In some embodiments, an exogenous α-ketoglutarate is cell permeable. In some embodiments, the α-ketoglutarate compound is dimethyl α-ketoglutarate (DM-αKG).

In some embodiments, the cell culture medium further comprises a mitogen activated protein kinase (MAPK) inhibitor. In some embodiments, the cell culture medium further comprises a glycogen synthase kinase 3β (GSK3β) inhibitor. In some embodiments, the cell culture medium further comprises a mitogen activated protein kinase (MAPK) inhibitor and a glycogen synthase kinase 3β (GSK3β) inhibitor. In some embodiments, no exogenous glutamine is added to the medium.

In some embodiments, systems and methods for inhibiting cell proliferation or facilitating differentiation are provided. In some embodiments, the methods comprise steps of providing a cell culture comprising mammalian stem cells in a medium; and maintaining α-ketoglutarate to succinate levels in the cells. In some embodiments an exogenous succinate compound is added to the medium. In some embodiments, the exogenous succinate compound is cell permeable. In some embodiments, the succinate is dimethyl succinate (DM-succinate).

In some embodiments, the invention provides a culture comprising stem cells and a medium; wherein the medium comprises an α-ketoglutarate compound, a MAPK inhibitor, and a GSK3β inhibitor.

In some embodiments, the invention provides systems and methods for inhibiting proliferation of dividing cells. In some embodiments, the methods comprise administering an agent that decreases intracellular levels of α-ketoglutarate. In some embodiments, the methods comprise administering an agent that increases intracellular levels of succinate. In some embodiments, the methods comprise further administering a glutamine synthase inhibitor.

The amount of each compound, activator or inhibitor can vary and be determined for optimum advantage depending on the precise culture conditions, specific inhibitors used, and type of cell cultured.

In some embodiments, inhibitors of GSK3β include antibodies to, dominant negative variants of and antisense nucleic acids that target GSK3. Specific examples of GSK3 inhibitors include, but are not limited to, CHIR99021, CHIR98014, AR-AO 14418 (see, e.g., Gould, et al, The International Journal of Neuropsychopharmacology 7:387-390 (2004)), CT 99021 (see, e.g., Wagman, Current Pharmaceutical Design 10:1105-1137 (2004)), CT 20026 (see, Wagman, supra), SB216763 (see, e.g., Martin, et al, Nature Immunology 6:111-IM (2005)), AR-A014418 (see, e.g., Noble, et al, PNAS 102:6990-6995 (2005)), lithium (see, e.g., Gould, et al, Pharmacological Research 48: 49-53 (2003)), SB 415286 (see, e.g., Frame, et al, Biochemical Journal 359:1-16 (2001)) and TDZD-8 (see, e.g., Chin, et al, Molecular Brain Research, 137(1-2): 193-201 (2005)). Further exemplary GSK3 inhibitors available from Calbiochem (see, e.g., Dalton, et al, WO2008/094597, herein incorporated by reference), include but are not limited to BIO (2'Z,3'£)-6-Bromoindirubin-3'-oxime (GSK3 Inhibitor IX); BIO-Acetoxime (2'Z,3'E)-6-Bromoindirubin-3'-acetoxime (GSK3 Inhibitor X); (5-Methyl-1H-pyrazol-3-yl)-(2-phenylquinazolin-4-yl)amine (GSK3-Inhibitor XIII); Pyridocarbazole-cyclopenadienylruthenium complex (GSK3 Inhibitor XV); TDZD-8 4-Benzyl-2-methyl-1,2,4-thiadiazolidine-3,5-dione (GSK3beta Inhibitor I); 2-Thio(3-iodobenzyl)-5-(1-pyridyl)-[1,3,4]-oxadiazole (GSK3beta Inhibitor II); OTDZT 2,4-Dibenzyl-5-oxothiadiazolidine-3-thione (GSK3beta Inhibitor III); alpha-4-Dibromoacetophenone (GSK3beta Inhibitor VII); AR-AO 14418 N-(4-Methoxybenzyl)-N'-(5-nitro-1,3-thiazol-2-yl)urea (GSK-3beta Inhibitor VIII); 3-(l-(3-Hydroxypropyl)-1H-pyrrolo[2,3-b] pyridin-3-yl]-4-pyrazin-2-yl-pyrrole-2,5-dione (GSK-3beta Inhibitor XI); TWS1 19 pyrrolopyrimidine compound (GSK3beta Inhibitor XII); L803 H-KEAPP APPQSpP-NH2 or its Myristoylated form (GSObeta Inhibitor XIII); 2-Chloro-1-(4,5-dibromo-thiophen-2-yl)-ethanone (GSK3beta Inhibitor VI); AR-AO144-18; SB216763; and SB415286. Residues of GSK3b that interact with inhibitors have been identified. See, e.g., Bertrand et al., J Mol Biol. 333(2): 393-407 (2003).

In some embodiments, inhibition of MAPK signaling comprises use of one or more agents, including small molecule inhibitors, inhibitory polynucleotides such as RNAi, antisense oligonucleotides; and the like. See, for example, Schindler et al. (2007) J. Dental Res. 86:800; Kumar et al. (2003) Nature Reviews 2:717; and Zheng et al. (2007) Trends in Pharmacological Sciences 28:286, each herein specifically incorporated by reference. Classes of inhibitors include non-diaryl heterocycle compounds (see Cirillo et al. (2002) Curr. Top. Med. Chem. 2(9):1021-1035); imidazole-based and pyrido-pyrimidin-2-one compounds (see Natarajan et al. (2005) Curr. Top. Med. Chem. 5(10): 987-1003); anti-oxidants (see Sadowska et al. (2007) Pulm Pharmacol Ther. 20(1):9-22); next generation inhibitors (see Zhang et al. (2007) Trends Pharmacol Sci. 28(6):286-95), each herein specifically incorporated by reference. Other inhibitors of the pathway may target inflammatory cytokines that upregulate p38 activation such as TNF, IL-1 and others (see Silva et al. (2010) Immunotherapy 2(6):817-833; Furst et al. (2005) Ann Rheum Dis. 64 Suppl 4:iv2-14); antisense and interfering oligonucleotides; activators of/ecotopic expression of protein phosphatases that de-phosphorylate p38 (e.g. mitogen-activated protein kinase phosphatase-7); expression of dominant-negative forms of the upstream adapters in the p38 pathway (e.g. dominant negative MKK3 or MKK6 or ASK1); and the like. p38 inhibitors can be small molecules, siRNA (e.g., US2005/0239731; WO 04/097020; WO 03/072590), antisense molecules, proteins, ribozymes or antibodies.

The compositions, systems, and methods for maintaining pluripotency and/or self-renewing characteristics, or for promoting cell differentiation, described herein are applicable to any stem cell or progenitor cell. As an illustrative example, any culture of ESC or iPSC or a respective cell line may be used in the respective method. Means of deriving a population of such cells are well established in the art (cf. e.g. Thomson, J. A. et al. [1998] Science 282, 1145-1147 or Cowan, C A. et al. [2004] JV. Engl. J. Med. 350, 1353-1356). Where the method is intended to be used for a progenitor cell, any progenitor cell may be used in this method of the disclosure. Examples of suitable progenitor cells include, but are not limited to, neuronal progenitor cells, endothelial progenitor cell, erythroid progenitor cells, cardiac progenitor cells, oligodendrocyte progenitor cells, retinal progenitor cells, or hematopoietic progenitor cells. Methods of obtaining progenitor cells are well known in the art. As two illustrative examples, a method of obtaining megakaryocyte progenitor cells has been disclosed in US patent application 2005/0176142 and a method of obtaining mouse liver progenitor cell lines has been described by Li et al. ((2005) Stem Cell Express, doi:10.1634/stemcells.2005-0108).

The compositions, systems, and methods described herein are also applicable to tissue-specific stem cells or progenitor cells, such as neural, hematopoietic and mesencyhemal cell. Cultured cell populations include heterogeneous as well as substantially homogenous populations. Cells cultured according to the methods described herein achieve, maintain, or have enhanced potency (differentiation capacity) Cell populations may contain mixed cell types with cells having different potencies (e.g., some are committed to a single lineage, others to two lineages, still others to all three lineages). Populations maybe restricted to single lineage cells so that all of the cells are endodermal progenitors, for example. Or there could be mixed populations where there are two or more types of single-lineage progenitors, for example, endodermal and mesodermal progenitors.

Stem cells or progenitor cells can be maintained and expanded in culture medium that is available to the art. Such media include, but are not limited to Dulbecco's Modified Eagle's Medium® (DMEM), DMEM F12 Medium®, Eagle's Minimum Essential Medium®, F-12K Medium®, Iscove's Modified Dulbecco's Medium®, RPMI-1640 Medium®. Many media are also available as a low-glucose formulation, with or without sodium pyruvate. Also contemplated is supplementation of cell culture medium with mammalian sera. Sera often contain cellular factors and components that are needed for viability and expansion. Examples of sera include fetal bovine serum (FBS), bovine serum (BS), calf serum (CS), fetal calf serum (FCS), newborn calf serum (NCS), goat serum (GS)3 horse serum (HS), human serum, chicken serum, porcine serum, sheep serum, rabbit serum, serum replacements, and bovine embryonic fluid. It is understood that sera can be heat-inactivated at about 55-65° C. if desirable to inactivate components of the complement cascade. Additional supplements can also be used advantageously to supply the cells with the trace elements for optimal growth and expansion. Such supplements include insulin, transferrin, sodium selenium and combinations thereof. These components can be included in a salt solution such as, but not limited to Hanks' Balanced Salt Solution® (HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids, however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine and L-valine. It is well within the skill of one in the art to determine the proper concentrations of these supplements.

Antibiotics are also typically used in cell culture to mitigate bacterial, mycoplasmal and fungal contamination. Typically, antibiotics or anti-mycotic compositions used are mixtures of penicillin/streptomycin, but can also include, but are not limited to, amphotericin (Fungizone®), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin and zeocin.

Hormones can also be advantageously used in cell culture and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine and L-thyronine. Lipids and lipid carriers can also be used to supplement cell culture media, depending on the type of cell and the fate of the differentiated cell. Such lipids and carriers can include, but are not limited to, cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others.

Also contemplated is the use of feeder cell layers. Feeder cells are used to support the growth of fastidious cultured cells, including stem cells. Feeder cells are normal cells that have been inactivated by γ-irradiation. In culture, the feeder layer serves as a basal layer for other cells and supplies cellular factors without further growth or division of their own (Lim, J. W. and Bodnar, A., 2002). Examples of feeder layer cells are typically human diploid lung cells, mouse embryonic fibroblasts, Swiss mouse embryonic fibroblasts, but can be any post-mitotic cell that is capable of supplying cellular components and factors that are advantageous in allowing optimal growth, viability and expansion of cells. In many cases, feeder cell layers are not necessary to keep the ES cells in an undifferentiated, proliferative state, as leukemia inhibitory factor (LIF) has anti-differentiation properties. Therefore, supplementation with LIF could be used to maintain non-embryonic cells in an, undifferentiated state. Additionally, a GSK-3 inhibitor and a MAPK inhibitor may be used to maintain cells in an undifferentiated state.

Cells in culture can be maintained either in suspension or attached to a solid support, such as extracellular matrix components and synthetic or biopolymers. Cells sometimes require additional factors that encourage their attachment to a solid support, such as type I, type II and type IV collagen, concanavalin A, chondroitin sulfate, fibronectin, "superfibronectin" and fibronectin-like polymers, gelatin, laminin, poly-D and poly-L-lysine, thrombospondin and vitronectin. The maintenance conditions of non-embryonic cells can also contain cellular factors that allow the cells, such as ESCs or iPSCs, to remain in an undifferentiated form. It is advantageous under conditions where the cell must remain in an undifferentiated state of self-renewal for the medium to contain epidermal growth factor (EGF), platelet derived growth factor (PDGF), leukemia inhibitory factor (LIF; in selected species), a GKS-3 inhibitor, a MAPK inhibitor or combinations thereof. It is apparent to those skilled in the art that supplements that allow the cell to self-renew but not differentiate should be removed from the culture medium prior to differentiation. Cells can benefit from co-culturing with another cell type. Such co-culturing methods arise from the observation that certain cells can supply yet-unidentified cellular factors that allow the cell to differentiate into a specific lineage or cell type. These cellular factors can also induce expression of cell-surface receptors, some of which can be readily identified by monoclonal antibodies. Generally, cells for co-culturing are selected based on the type of lineage one skilled in the art wishes to induce, and it is within the capabilities of the skilled artisan to select the appropriate cells for co-culture.

Methods of identifying and subsequently separating differentiated cells from their undifferentiated counterparts can be carried out by methods well known in the art. Cells that have been induced to differentiate can be identified by selectively culturing cells under conditions whereby differentiated cells outnumber undifferentiated cells. Similarly, differentiated cells can be identified by morphological changes and characteristics that are not present on their undifferentiated counterparts, such as cell size, the number of cellular processes (i.e., formation of dendrites or branches), and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS) and enzyme-linked immunosorbent assay (ELISA). From the standpoint of transcriptional upregulation of specific genes, differentiated cells often display levels of gene expression that are different from undifferentiated cells. Reverse-transcription polymerase chain reaction (RT-PCR) can also be used to monitor changes in gene expression in response to differentiation. Alternatively or additionally, whole genome analysis using microarray technology can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads, and combinations thereof. A preferred embodiment of the disclosure envisions the use of FACS to identify and separate cells based on cell-surface antigen expression.

Described herein are compositions comprising stem cells or progenitor cells in combination with at least one agent that modulates α-ketoglutarate and succinate levels, wherein said cells can differentiate into cell types of more than one lineage. In some embodiments, the compositions comprise cells in culture medium. In some embodiments, the compositions comprise an in vitro population of cells. In some embodiments, the compositions comprise an ex vivo population of cells. In some embodiments, the compositions comprise an in vivo population of cells. The invention also provides a system for preparing a composition comprising admixing stem cells or progenitor cells with at least one agent that modulates α-ketoglutarate and succinate levels, and optionally admixing a carrier (e.g., cell culture medium or a pharmaceutically acceptable carrier), wherein said cells can differentiate into cell types of more than one embryonic lineage.

Culture vessels the cells in the media include, but are not limited to the following: flask, flask for tissue culture, dish, petri dish, dish for tissue culture, multi dish, micro plate, micro-well plate, multi plate, multi-well plate, micro slide, chamber slide, tube, tray, CellSTACK® Chambers, culture bag, and roller bottle. The cells may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, 2000 ml or any range derivable therein, depending on the needs of the culture. In a certain embodiment, the culture vessel may be a bioreactor, which may refer to any device or system that supports a biologically active environment. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel can be cellular adhesive or non-adhesive and selected depending on the purpose. The cellular adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). Substrates for cell adhesion may include collagen, gelatin, poly-L-lysine, poly-D-lysine, laminin, and fibronectin and mixtures thereof, Matrigel™, and lysed cell membrane preparations (Klimanskaya et al., 2005).

Other culturing conditions can be appropriately applied. For example, the culturing temperature can be about 30 to 40° C., for example, at least or about 31, 32, 33, 34, 35, 36, 37, 38, 39° C. The $CO_2$ concentration can be about 1 to 10%, for example, about 2 to 5%, or any range derivable therein. The oxygen tension can be at least or about 1, 5, 8, 10, 20%, or any range derivable therein.

In some embodiments, the invention provides cell culture media for culturing cells according to methods of the present invention.

In some embodiments, the invention provides compositions, systems, and methods for enriching a population of cells for pluripotent cells. In some embodiments, the method comprises contacting a mixed population of cells with an α-ketoglutarate compound or an agent that increases α-ketoglutarate relative to succinate levels in the cells. In some embodiments, no exogenous glutamine is added to the medium. In some embodiments, pluripotent cells are be selected from cells that are not pluripotent because the former has higher proliferation rate compared to the latter. In some embodiments, pluripotent cells can be selected from cells that are not pluripotent cells because the former has higher survival rate compared to the latter. In some embodiments, the invention provides compositions, systems, and methods for enriching pluripotent cells to at least 50%, 60%, 70%, 80%, 90%, 95%, or 99% of the total population of cells.

In some embodiments, the invention provides compositions, systems, and methods for enriching a population of cells for stem cells or progenitor cells. In some embodiments, the method comprises contacting a mixed population of cells with a medium that has significantly reduced levels of glutamine. In some embodiments, no exogenous glutamine is added to the medium.

For pluripotent cells to be enriched, the percentage of non-pluripotent cells is preferably not more than 50%, not more than 40%, not more than 30%, not more than 20%, not more than 10%, not more than 5%, or more preferably not more than 1% of the total cell population. Markers for pluripotent cells can be used to evaluate the percentage of cells as pluripotent cells according to methods known in the art, e.g., fluorescent staining and imaging of pluripotency markers or FACS analysis.

Epigenetic Control

The inventors found that modulating αKG:succinate levels in cells specifically affects certain epigenetic changes. It is suggested that methylation of histone plays an important role in heterochromatin formation, inactivation of X-chromosome, genomic imprinting, repair of DNA damage and regulation of gene transcription, and that methylation sites of histone are highly conserved among different species, and cells with different differentiation potentials have different profiles of methylation modification of histone.

α-ketoglutarate metabolism may be manipulated to modulate epigenetic changes in cells. In some embodiments, the invention provides systems and methods for epigenetic control of cell proliferation or differentiation. In some embodiments, the methods comprise administering an agent that decreases intracellular levels of α-ketoglutarate to regulate chromatin modifications. In some embodiments, the methods comprise administering an agent that decreases intracellular levels of α-ketoglutarate to regulate H3K27me3 and Ten eleven translocation (Tet)-dependent DNA demethylation. In some embodiments, the methods comprise administering an agent that increases intracellular levels of succinate to regulate chromatin modifications. In some embodiments, the methods comprise administering an agent that increases intracellular levels of succinate to regulate H3K27me3 and Ten eleven translocation (Tet)-dependent DNA demethylation. In some embodiments, the methods comprise further administering a glutamine synthase inhibitor.

In addition to histone modifications, in some embodiments, the invention provides compositions, systems, and methods for modulating DNA methylation in a cell. In some embodiments, the invention describes contacting the cell with an α-ketoglutarate compound or an agent that increases cellular α-ketoglutarate relative to succinate levels in the cell.

DNA methylation is known to play a key role in various phenomena, such as tissue-specific gene expression, imprinting, X chromosome inactivation, and carcinogenesis. Congenital or acquired diseases resulting from abnormalities of the DNA methyltransferase gene or the DNA methylation status and abnormalities of DNA methylation in cloned animals have been known.

A variety of methods have been used to identify DNA methylation in cells. For example, one method involves restriction landmark genomic scanning (Kawai et al., Mol. Cell. Biol. 14:7421-7427, 1994), and another example involves methylation-sensitive arbitrarily primed PCR (Gonzalgo et al., Cancer Res. 57:594-599, 1997). Changes in methylation patterns at specific CpG sites have been monitored by digestion of genomic DNA with methylation-sensitive restriction enzymes followed by Southern analysis of the regions of interest (digestion-Southern method). Another method for analyzing changes in methylation patterns involves a PCR-based process that involves digestion of genomic DNA with methylation-sensitive restriction enzymes prior to PCR amplification (Singer-Sam et al., Nucl. Acids Res. 18:687,1990).

Therapeutic Use

In some embodiments, the invention provides compositions, systems, and methods for treating a patient with cancer. The inventors have found that cell proliferation and differentiation can be manipulated by controlling αKG: succinate levels. The present disclosure demonstrates, among other things, that decreased αKG:succinate levels can inhibit cell proliferation. In some embodiments, the present disclosure describes compositions and systems for controlling αKG:succinate levels that would promote cell differentiation.

In some embodiments, compositions and systems of the present disclosure can be used in vivo to treat cancers, (e.g., including, but not limited to, lymphoma, leukemia, prostate cancer, lung cancer, stomach cancer, pancreatic cancer, breast cancer, and colon cancer). In the case where a method of the present invention is carried out in vivo, for example, where the cancer cells are present in a human subject, contacting can be carried out by administering one or more doses of a therapeutically effective amount of an agent that reduces relative αKG:succinate levels to the human subject (e.g., by directly injecting the compound into a tumor, by targeted delivery such as nanoparticles, or through systemic administration).

In some embodiments, the invention provides composition, systems, and methods to restore the population of certain cells in a patient, e.g., certain stem cells. For example, cancer treatment to eradicate a patient's cancer cell population may eliminate the patient's bone marrow stem cells. A return of the patient's own or a donor's stored stem cells to the patient may supplement or repopulate the patient's in vivo pool of hematopoietic stem cells. The method may increase the number of hematopoietic stem cells and mobilize these cells from the bone marrow to the bloodstream and may allow the use of greater doses of cancer treatments such as chemo- or radiotherapy, but with less risk than bone marrow transplantation.

In some embodiments, the invention provides compositions, systems, and methods for autologous or heterologous stem cell population transplant. For example, stem cells originated from cells obtained from a patient or other donor can be cultured using systems and compositions of the present invention. The compositions may be administered to a patient before, after, or while undergoing cancer treatment and/or may be administered to a donor.

In one non-limiting example of such applications, blood or peripheral white blood cells, which may comprise a stem cell population comprising hematopoietic stem cells, may be isolated from the patient. The cells may be isolated from the patient after administering the composition and prior to cancer treatment. The autologous stem cell population may be stored for future use. The stem cell population may later be administered to the patient who has previously undergone a cancer treatment. In addition, the stored autologous stem cells may be used in transplants. Such treatment may enhance the success of transplantation before, during, and following immunosuppressive treatments.

EXAMPLES

The following examples are provided for illustration and are not in any way to limit the scope of the invention.

Example 1

GSK3B and ERK Inhibitors in 2i-Containing Medium Confer Glutamine Independence in Cell Culture Pluripotent cells of the inner cell mass (ICM) of pre-implantation blastocysts exist only transiently but with appropriate media formulations can be expanded without significant differentiation in vitro[1,2]. In particular, mESCs can be maintained in two previously established medium formulations: one a serum-free medium reported to support a cellular phenotype that mimics "naïve" epiblast cells of the ICM (2i/LIF or 2i/L) and a second serum-based medium that supports the proliferation of a more committed ES cell phenotype (serum/LIF or S/L)[3-10]. To characterize ES cell metabolism, the inventors investigated whether cells cultured in these two growth media exhibit different patterns of dependency on glucose and/or glutamine (FIG. 1a and FIG. 5a-c). In most mammalian cells, glucose is the main carbon source that supports bioenergetics and macromolecular synthesis while glutamine supplies the proliferating cell with reduced nitrogen and maintains tricarboxylic acid (TCA) cycle anaplerosis. ESCs cultured in either medium proliferated at equivalent rates when glucose and glutamine were abundant and cells cultured with or without 2i were unable to proliferate in the absence of glucose (FIG. 5a,b). In contrast, cells cultured in 2i/L medium proliferated robustly in the absence of exogenous glutamine, while cells cultured in S/L medium could not (FIG. 1a and FIG. 5c).

Figure 1F:
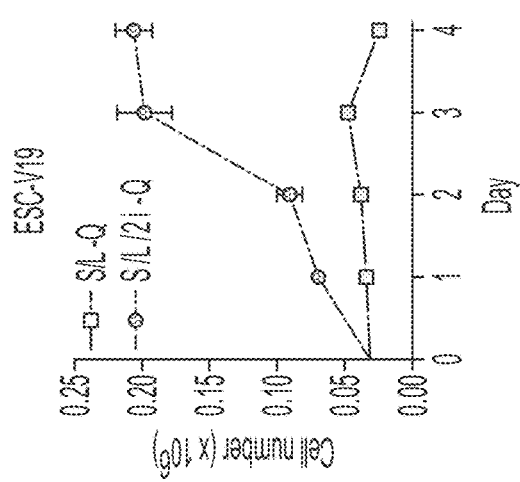
Figure 1E:
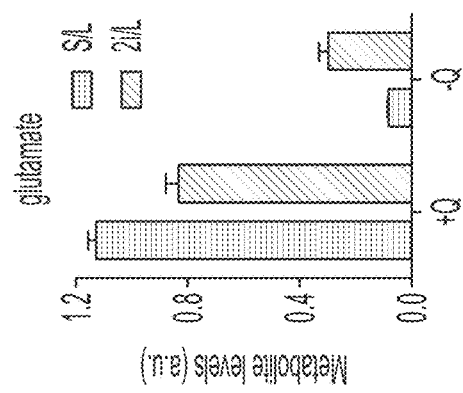
Figure 5E:
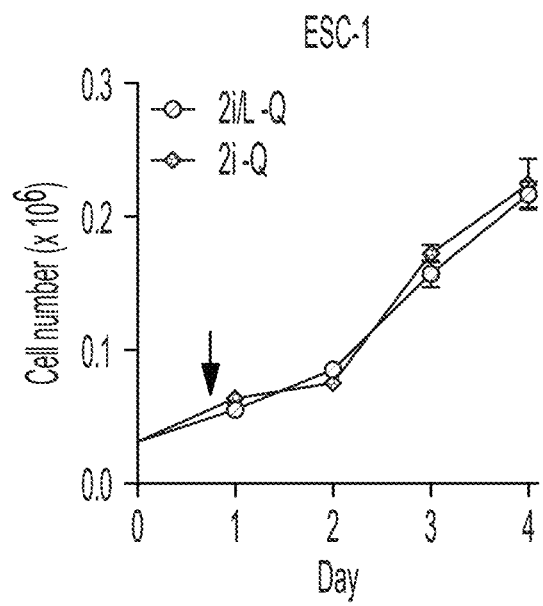
Figure 5F:
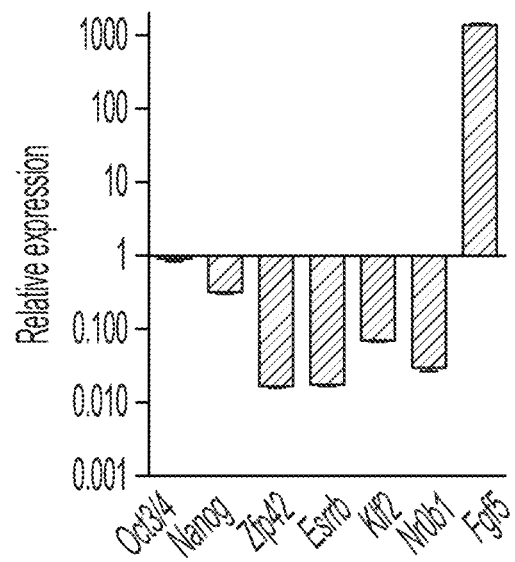
Figure 5G:
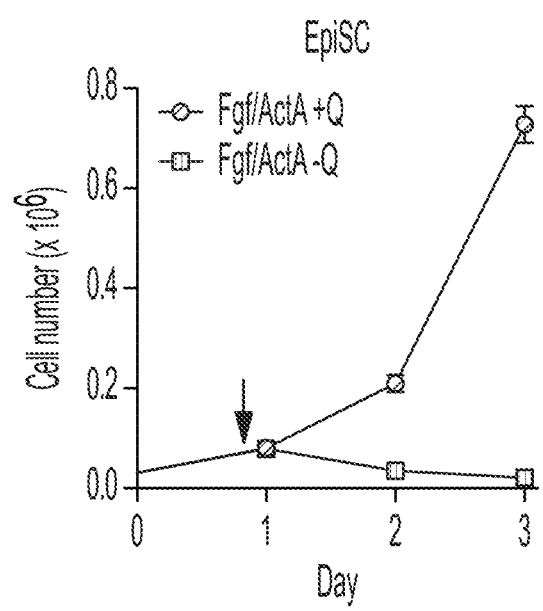
Figure 5H:
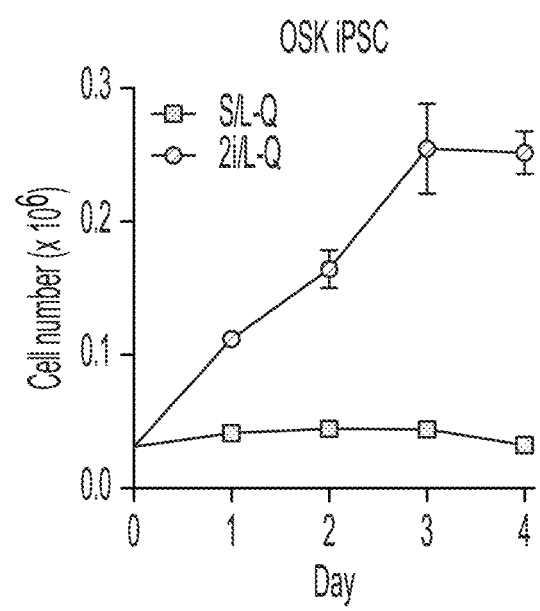

The above results were surprising because with the exception of rare cancer cell lines, mammalian cells are unable to be propagated in tissue culture without glutamine supplementatio[11]. To test the reproducibility of this phenotype, the inventors generated four additional V6.5 ESC lines (ESC-1-4). All cell lines exhibited robust glutamine-independent proliferation in 2i/L medium while retaining features of pluripotent cells, including ESC-like morphology, reactivity to alkaline phosphatase (AP) and the ability to form teratomas in vivo (FIG. 1b,c, FIG. 5d). Cells cultured in 2i medium alone could also proliferate in the absence of exogenous glutamine (FIG. 5e). This effect was not due to minor differences in medium nutrient formulations as supplementing serum/LIF medium with GSK3B and ERK inhibitors present in 2i medium also enabled glutamine-independent proliferation while maintaining ESC morphology and markers of pluripotency (FIG. 1d,e). An alternative ESC media used in some laboratories as a substitute for serum/LIF medium has BMP4 and LIF added to the same serum-free formulation as in 2i/LIF[12]. This BMP4/LIF medium failed to support glutamine-independent growth (FIG. 1f). Likewise, epiblast stem cells (EpiSCs), which represent post-implantation pluripotency and are propagated in serum-free medium containing FGF2 and Activin A, could not proliferate in the absence of exogenous glutamine (FIGS. 5f,g). However, the ability to undertake glutamine-independent growth was not limited to embryonic pluripotency; fibroblast-derived induced pluripotent cell (iPSC) lines were also able to proliferate in glutamine-free 2i/L medium (FIG. 5h). Together, these results indicate that the GSK3B and ERK inhibitors in 2i-containing medium enable proliferation of pluripotent cells in the absence of exogenous glutamine.

Figure 1G:
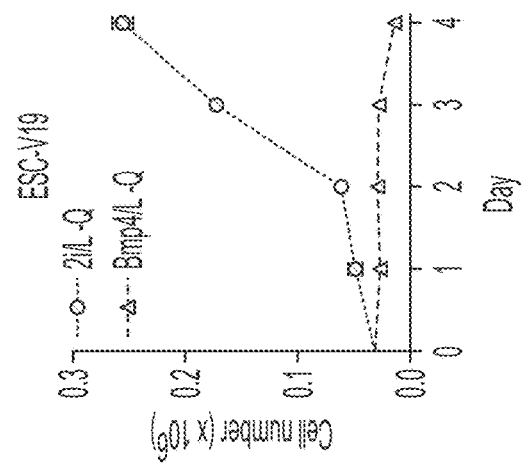
Figure 5I:
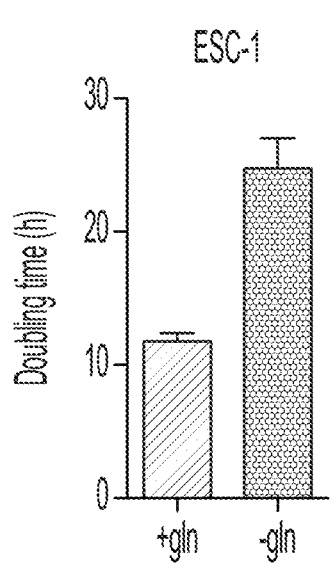
Figure 5J:
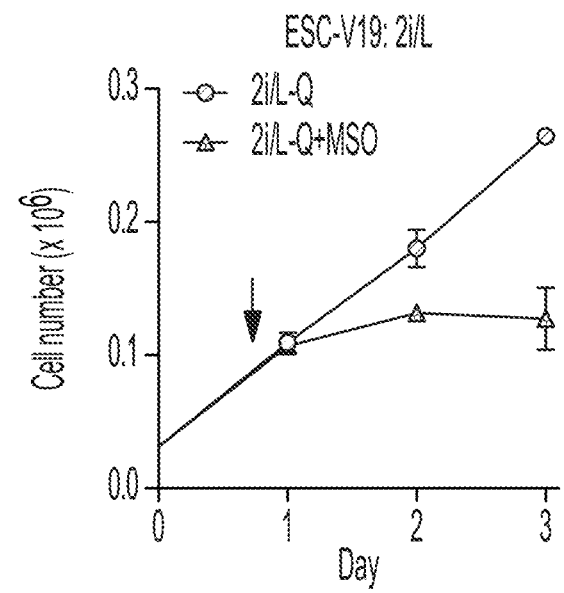
Figure 5K:
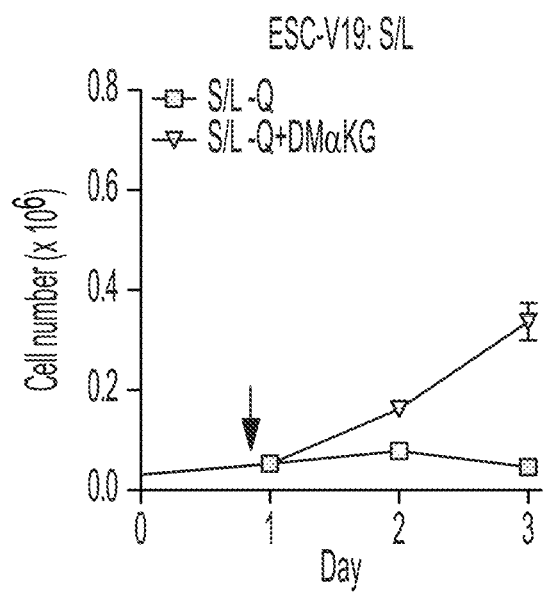
Figure 5L:
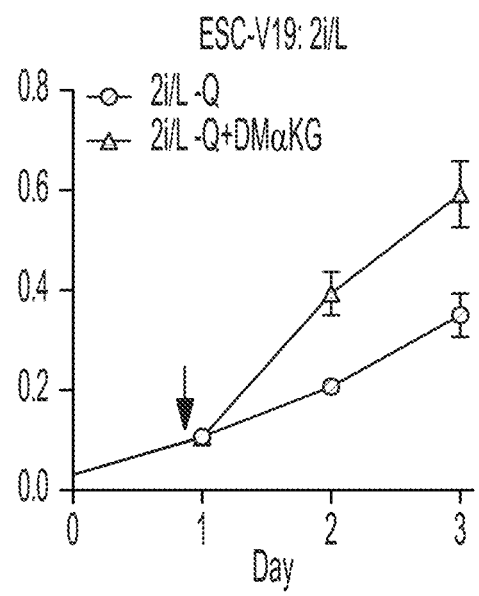

As glutamine is the obligate nitrogen donor for nucleotide synthesis, the fact that cells proliferated in the absence of exogenous glutamine in 2i/L medium, albeit at a slower rate than cells cultured in glutamine-replete medium (FIG. 5i), indicates that these cells must be capable of de novo glutamine synthesis. Indeed, chemical inhibition of glutamine synthase was sufficient to block proliferation of cells in glutamine-free 2i/L medium (FIG. 5j). Likewise, addition of cell-permeable dimethyl-α-ketoglutarate (DM-αKG), which can serve as a precursor for glutamine synthesis, was sufficient to enable glutamine-independent proliferation in both S/L and 2i/L conditions (FIG. 5k), suggesting that the supply of metabolic precursors for glutamine synthesis determines the ability of pluripotent stem cells to proliferate in the absence of glutamine. In support of this model, intracellular pools of glutamate, the immediate precursor of glutamine, underwent dramatic (~10-fold) depletion within 8 hours of glutamine withdrawal in S/L conditions (FIG. 1g). In contrast, 2i/L cells exhibited significantly higher glutamate ($p<0.0005$) levels following glutamine withdrawal (FIG. 1g). These results suggest that 2i/L cells can generate glutamate (and glutamine) from carbon sources other than glutamine itself.

Figure 2A:
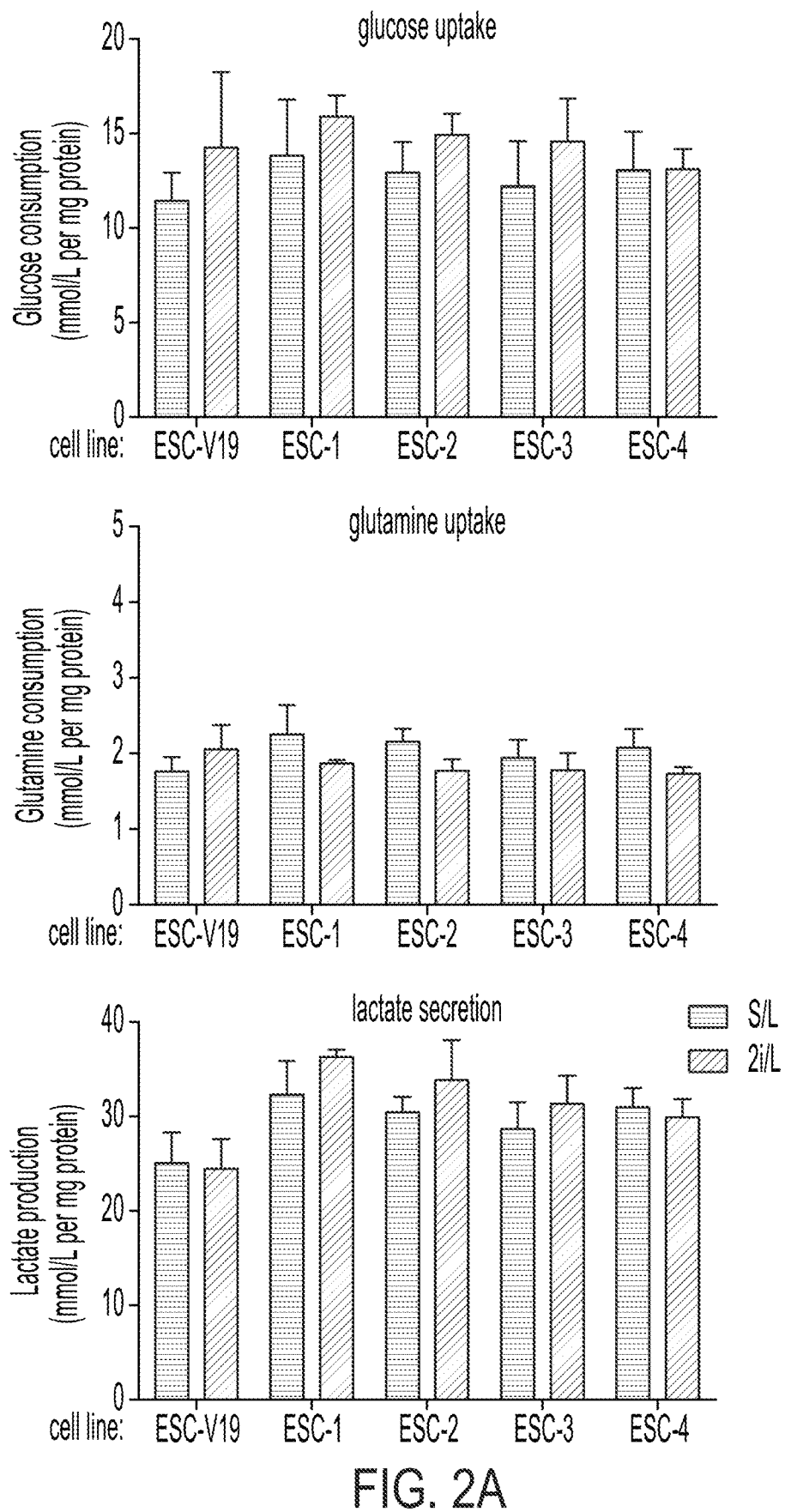
FIGS. 2A to 2G show bar graphs and line graphs analyzing cellular metabolites and kinetics.
Figure 2B:
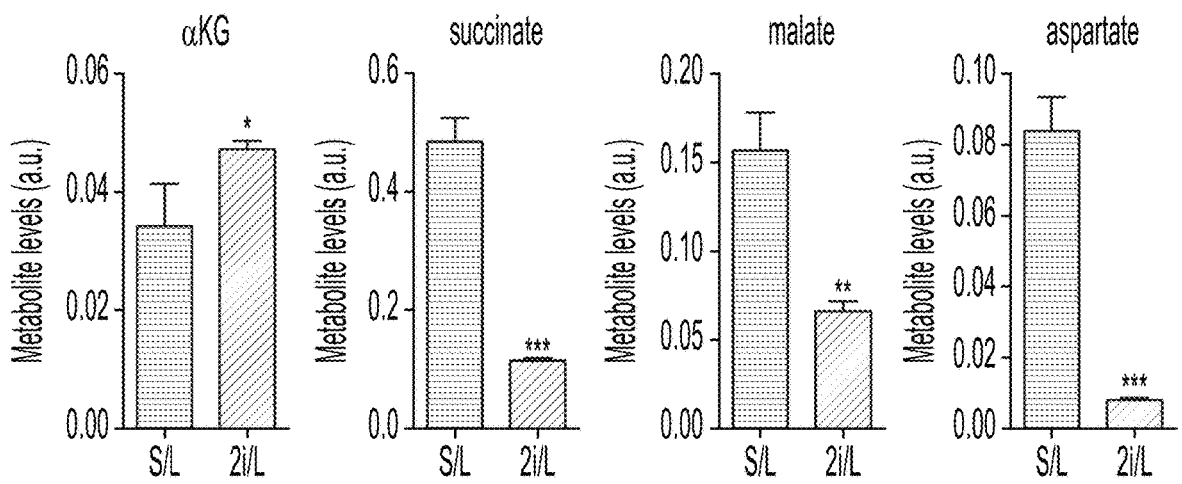

To elucidate how 2i/L supports glutamine-independent cell growth, the inventors measured the uptake of the two most abundant metabolites in the medium, glucose and glutamine. Cells cultured in both S/L and 2i/L consumed high levels of glucose and glutamine, while excreting similar levels of lactate, consistent with the metabolic profile of most proliferating cells, including cancer cells and pluripotent cells (FIG. 2a)[13,14]. Even as they produce large amounts of lactate, proliferating cells must generate the macromolecular precursors—including the nucleotides, amino acids and fatty acids—required to produce a daughter cell. Oxidation of glucose and glutamine via the mitochondrial TCA cycle provides a critical source of these biosynthetic precursors. The fact that 2i/L enabled ESCs to proliferate in the absence of glutamine indicates that 2i may alter TCA cycle dynamics. With the exception of α-ketoglutarate (αKG), steady-state levels of TCA cycle metabolites were reproducibly diminished in ESCs cultured in 2i/L (FIG. 2b).

Figure 2C:
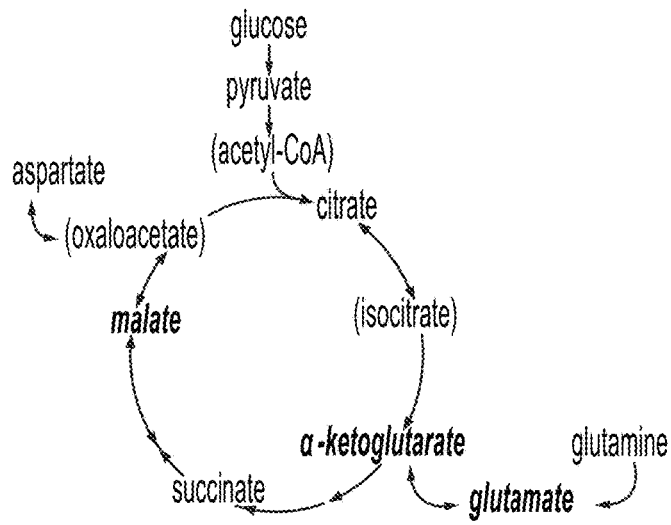
Figure 2D:
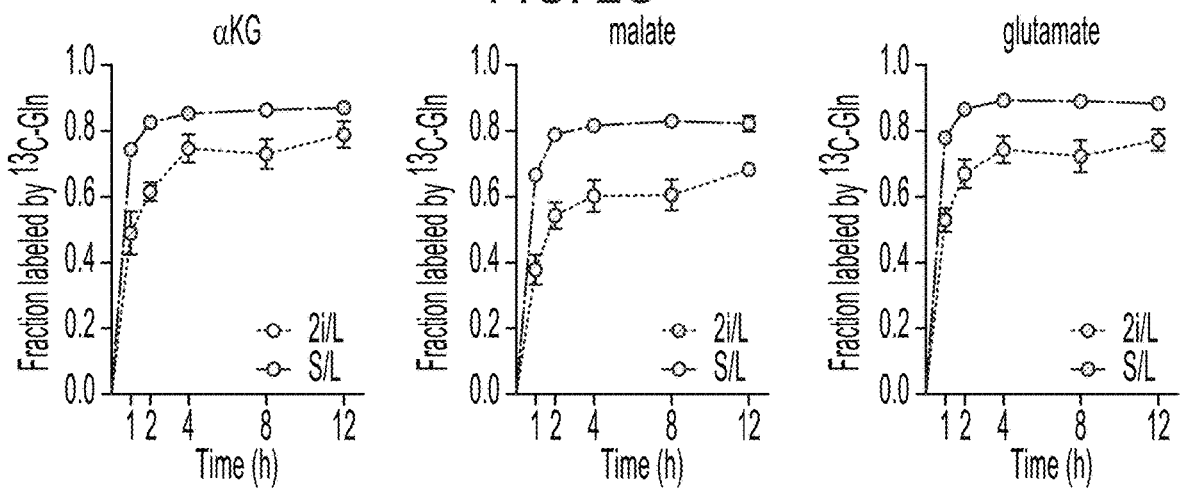
Figure 2E:
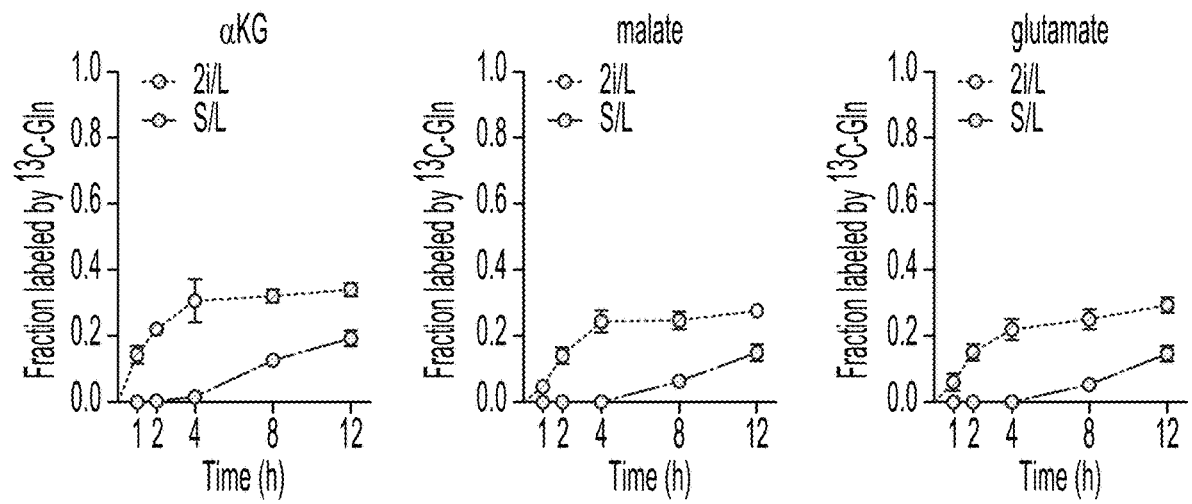
Figure 2F:
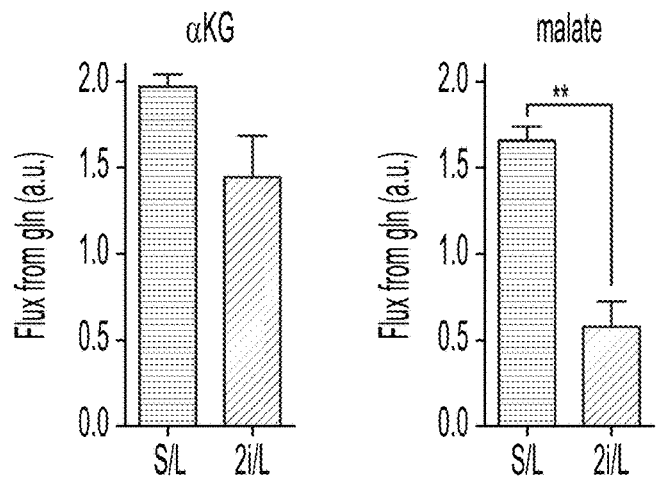
Figure 2G:
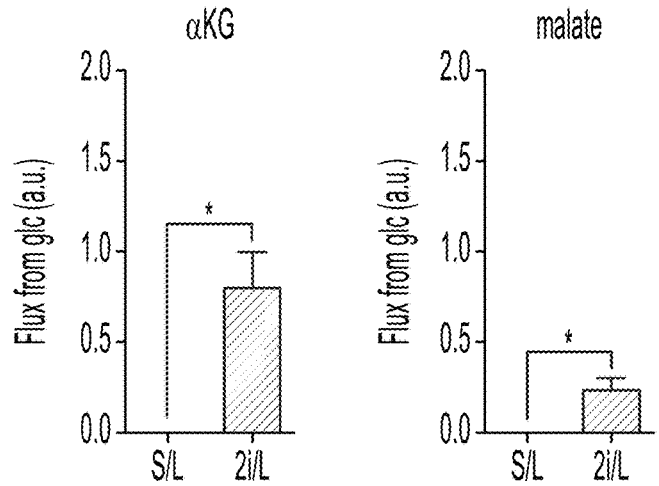

In most cells, glutamine is catabolized to αKG to support TCA cycle anaplerosis (FIG. 2c). ESCs grown in S/L medium exhibited high levels of TCA cycle intermediates and virtually all intracellular glutamate, αKG and malate were rapidly labeled following addition of [U-$^{13}$C]glutamine (FIG. 2d). In contrast, a substantial fraction of these metabolites failed to label with glutamine in ESCs grow in 2i/L. Instead, there was a rapid labeling of these three metabolites pools from [U-$^{13}$C]glucose (FIG. 2e). Quantification of metabolite fluxes revealed that although the flux of glutamine-derived carbons through αKG was similar in both conditions, glutamine flux through malate was significantly diminished in cells cultured in 2i/L, indicating that the entry of glutamine-derived αKG into the TCA cycle is repressed by culture in 2i/L (FIG. 2f). Instead, when cells are cultured in 2i/L, a substantial amount of both αKG and malate was produced from glucose (FIG. 2g).

Figure 6A:
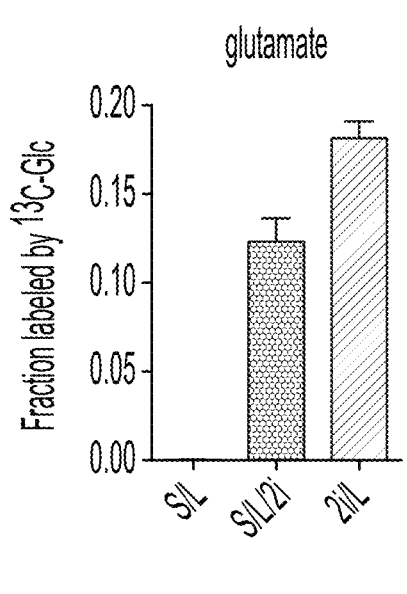
FIGS. 6A to 6D show FIG. 6A, Bar graph showing glutamate generated from glucose-derived carbons. ESC-1 cells were cultured for four hours in glutamine-free S/L or 2i/L medium containing [U-$^{13}$C]glucose and the total amount of glutamate labeled by glucose-derived carbons is shown.
Figure 6B:
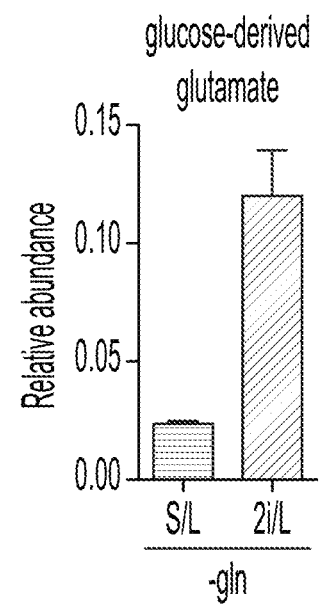
Figure 6C:
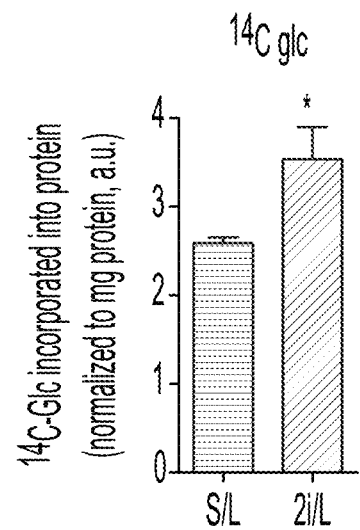
Figure 6D:
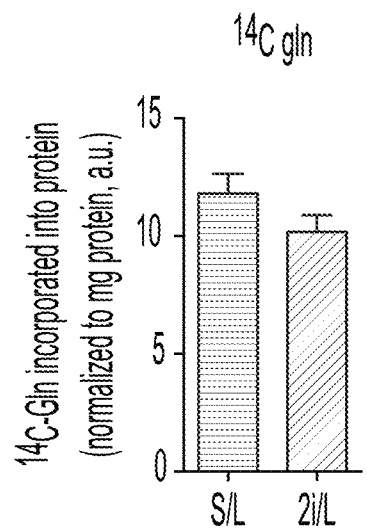

Together, these observations provided a potential explanation for the ability of cells cultured in 2i to proliferate in the absence of glutamine. Intracellular glutamate, which is the necessary precursor for de novo glutamine synthesis, is generated from αKG (FIG. 2c). Cells cultured with 2i inhibitors demonstrated substantial glucose-dependent glutamate production (FIG. 6a). Consequently, during conditions of glutamine depletion, cells cultured in 2i/L medium were able to use glucose-derived carbons to maintain elevated glutamate pools sufficient to support cell growth (FIG. 6b).

To further confirm that 2i promotes increased glucose-dependent amino acid synthesis, the relative incorporation of glucose- and glutamine-derived carbon into proteins was examined. By incubating cells with [U-$^{14}$C]glutamine or [U-$^{14}$C]glucose and then measuring the $^{14}$C signal in protein extracts, the inventors confirmed that in comparison to their S/L counterparts, 2i/L cells utilized more glucose-derived carbon and relatively less glutamine-derived carbon to support protein synthesis (FIG. 5c).

Materials and Methods:

Cell lines. ESC1-4 lines are V.65 (F1 C57BL6 X 129S4/SvJae) mESCs. Tet1/2 double knockout ES cells,[1] V19 ES cells (ESC-V19) and OKS iPSC[2] were a kind gift from Rudolf Jaenisch (MIT/Whitehead Institute Cambridge, Mass. USA). V6.5 ESCs #1-4 were derived from E3.5 blastocysts following standard ES cell isolation procedures[3]. Flushed blastocysts were plated onto laminin-coated dishes (20 μg/ml, Stemgent 06-0002) in 2i/LIF medium. Mice were purchased from Jackson Labs, Bar Harbor, Me. (C57BL/6 JAX, 000664 and 129S4/SvJae JAX 009104).

Cell culture. Maintenance media for ES cells were as follows: serum/LIF (S/L) maintenance medium contained Knockout DMEM (Gibco) supplemented with 15% ESC-qualified FBS (Gemini), penicillin/streptomycin (Life Technologies), 0.1 mM 2-mercaptoethanol, L-glutamine (2 mM, Life Technologies) and leukemia inhibitory factor (LIF) plated onto irradiated feeder mouse embryonic fibroblasts (MEFs); 2i/LIF maintenance conditions used a base medium made from a 1:1 mix of DMEM/F12 (Life Technologies 11302-033) and Neurobasal (Life Technologies 21103-049) containing N2 and B27 supplements (Life Technologies 17502-048 and 17504-044, 1:100 dilutions), penicillin/streptromycin, 0.1 mM 2-mercaptoethanol, L-glutamine (2 mM), LIF, CHIR99021 at 3 μM (Stemgent) and PD0325901 at 1 μM (Stemgent). Experimental media utilized for all experiments (except growth curves with and without glucose, $^{13}$C isotope tracing experiments and $^{14}$C labeling experiments) contained 1:1 mix of glutamine-free DMEM (Life Technologies 11960-051) and Neurobasal (Life Technologies 21103-049) with or without 2 mM glutamine. With the exception of 15% dialyzed FBS (Gemini 100-108) in S/L experimental medium, all other supplements were equivalent to maintenance media (S/L or 2i/L). For growth curves with and without glucose, $^{13}$C isotope tracing experiments and $^{14}$C labeling experiments, medium contained 1:1 mix of glutamine- and glucose-free DMEM (Invitrogen A14430-01) and glutamine- and glucose-free Neurobasal (Invitrogen 0050128DJ) containing either 20 mM [U-$^{13}$C]glucose or 2 mM [U-$^{13}$C]glutamine (Cambridge Isotope Labs) and either 20 mM unlabeled glucose or 2 mM unlabeled glutamine as necessary; all supplements were the same as experimental media described above (S/L or 2i/L). All experiments were performed using feeder-free conditions. ESC-1 EpiSCs were cultured feeder-free on fibronectin (Sigma) coated plates in EpiSC maintenance medium including DMEM/F12, N2 and B27 supplements, penicillin/streptomycin, 0.1 mM 2-mercaptoethanol, L-glutamine, 75 μg/ml BSA (Gibco) supplemented with human activin A (20 ng/ml; Peprotech) and bFgf (10 ng/ml; Invitrogen). EpiSCs were passaged 1:2 or 1:4 using Accutase every other day. For ESC to EpiSC differentiation, ESC-1 cells were plated in fibronectcin-coated dishes. Twenty-four hours after plating the medium was changed to EpiSC maintenance medium supplemented with 6 μM JAK inhibitor (Calbiochem) for five passages. Analysis was performed on passage 7 EpiSCs. UTX/Jmjd3 inhibitors GSK-J4 and GSK-J5 were purchased from Tocris Bioscience.

Teratomas. ESC-1 cells were plated in maintenance medium at a concentration of 2.5×10$^5$ cells per T25 dish. The following day medium was changed to 2i/L experimental medium with or without glutamine. 72 hours later 1×10$^6$ cells were harvested from each group and mixed 1:1 with experimental medium (without glutamine) plus Matrigel Basement Membrane Matrix (BD) or experimental medium alone and injected into the flanks of recipient SCID mice. All conditions produced tumors in 4-8 weeks. Mice were euthanized before tumor size exceeded 1.5 cm in diameter. Tumors were excised and fixed in 4% paraformaldehyde overnight at 4° C. Tumors were paraffin-embedded and sections were stained with hematoxylin and eosin according to standard procedures by Histosery Inc.

Glucose, glutamine and lactate measurements. Glucose, glutamine and lactate levels in culture medium were measured using a YSI 7100 multichannel biochemistry analyzer (YSI Life Sciences). Fresh medium was added to 12-well plates of sub-confluent cells and harvested 48 hours later. Changes in metabolite concentrations relative to fresh media were normalized to protein content of each well.

Metabolite profiling. For all metabolite experiments, cells were seeded in their standard culture medium in 6-well plates and the next day were changed into experimental medium. Medium was changed again at the indicated time before harvest (usually 1-24 hours). Metabolites were extracted with 1 mL ice-cold 80% methanol supplemented with 20 μM deuterated 2-hydroxyglutarate (D-2-hydroxyglutaric-2,3,3,4,4-$d_5$ acid, d5-2HG) as an internal standard. After overnight incubation at −80° C., lysates were harvested and centrifuged at 21,000 g for 20 minutes to remove protein. Extracts were dried in an evaporator (Genevac EZ-2 Elite) and resuspended by incubation at 30° C. for 2 hours in 50 μL of 40 mg/mL methoxyamine hydrochloride in pyridine. Metabolites were further derivatized by addition of 80 μL of MSTFA +1% TCMS (Thermo Scientific) and 70 μl ethyl acetate (Sigma) and incubated at 37° C. for 30 minutes. Samples were analyzed using an Agilent 7890A GC coupled to Agilent 5975C mass selective detector. The GC was operated in splitless mode with constant helium gas flow at 1 mL/min. 1 μl of derivatized metabolites was injected onto an HP-5MS column and the GC oven temperature ramped from 60° C. to 290° C. over 25 minutes. Peaks representing compounds of interest were extracted and integrated using MassHunter software (Agilent Technologies) and then normalized to both the internal standard (d5-2HG) peak area and protein content of duplicate samples as determined by BCA protein assay (Thermo Scientific). Ions used for quantification of metabolite levels are as follows: d5-2HG m/z 354; KG, m/z 304; aspartate, m/z 334; citrate, m/z 465; glutamate, m/z 363; malate, m/z 335 and succinate, m/z 247. All peaks were manually inspected and verified relative to known spectra for each metabolite. For isotope tracing studies, experiments were set up as described above using glucose- and glutamine-free DMEM:NB media base supplemented with $^{12}$C-glucose (Sigma) and $^{12}$C-glutamine (Gibco) or the $^{13}$C versions of each metabolite, [U-$^{13}$C] glucose or [U-$^{13}$C]glutamine (Cambridge Isotope Labs). Enrichment of $^{13}$C was assessed by quantifying the abundance of the following ions: αKG, m/z 304-315; aspartate, m/z 334-346; citrate, m/z 465-482; glutamate, m/z 363-377 and malate, m/z 335-347. Correction for natural isotope abundance was performed using IsoCor software[4]. Flux was calculated as the product of the first order rate constant of the kinetic labeling curve and relative metabolite pool size (normalized to mean S/L values for each experiment)[5]. The flux from glucose- and glutamine-derived carbons was calculated for each of three independent experiments and the average total flux for each metabolite was shown.

Protein labeling. ES cells were plated at $7.5 \times 10^5$ per 6-well plate into experimental medium (S/L or 2i/L) containing 0.01% unenriched D-[U-$^{14}$C]-glucose (Perkin Elmer NEC042V250UC) or L-[U-$^{14}$C]-glutamine (Perkin Elmer NEC451050UC). 48 hours later, cells were washed with PBS, scraped and pelleted at 4° C. Protein pellets devoid of lipid fractions were isolated according to the Bligh-Dyer method[6]. Briefly, pellets were resuspended in 200 μL dH20, 265 μL 100% methanol and 730 μL of chloroform. Samples were vortexed for 1 hour at 4° C. The organic phase was removed and the remaining sample washed with 1× volume of methanol and spun 14,200 g for 5 minutes. The supernatant was discarded and pellet was resuspended in 6 M guanidine hydrochloride at 65° C. for 30-45 minutes. Samples were quantified using Beckman LS 60001C instrument. Values represent four independent wells normalized to protein of duplicate samples.

Growth curves. ESC or EpiSCs were plated in maintenance medium at a concentration of 375,000 cells per 12-well plate. The following day cells were washed with PBS and media were changed to experimental media (for S/L conditions this included dialyzed FBS) with or without individual metabolites. Cells were counted each day using a Beckman Coulter Multisizer 4.

qRT-PCR. RNA was isolated using the RNeasy kit (Qiagen). After DNase treatment, 1-2 μg RNA was used for cDNA synthesis using the First-Strand Synthesis kit (Invitrogen). Quantitative RT-PCR analysis was performed in biological triplicate using an ABI Prism 7000 (Applied Biosystems) with Platinum SYBR green.

| Gene | Forward primer 5'→3' | Reverse primer 5'→3' |
|---|---|---|
| Pou5f1 | (SEQ ID NO: 13) acatcgccaatcagc ttgg | (SEQ ID NO: 14) agaaccatactcgaa ccacatcc |
| Nanog | (SEQ ID NO: 15) aagatgcggactgtg ttctc | (SEQ ID NO: 16) cgcttgcacttcatc ctttg |
| Esrrb | (SEQ ID NO: 17) tttctggaacccatg gagag | (SEQ ID NO: 18) agccagcacctcctt ctaca |
| Klf2 | (SEQ ID NO: 19) taaaggcgcatctgc gtaca | (SEQ ID NO: 20) cgcacaagtggcact gaaag |
| Nr0b1 | SEQ ID NO: 21 tccaggccatcaaga gtttc | (SEQ ID NO: 22) atctgctgggttctc cactg |
| Fgf5 | (SEQ ID NO: 23) aaactccatgcaagt gccaaat | (SEQ ID NO: 24) tctcggcctgtcttt tcagttc |
| Zfp42 | (SEQ ID NO: 25) cgagtggcagtttct tcttgg | (SEQ ID NO: 26) cttcttgaacaatgc ctatgactcacttcc |

-continued

| Gene | Forward primer 5'→3' | Reverse primer 5'→3' |
|---|---|---|
| Actin | (SEQ ID NO: 27) tggcgcttttgactc aggat | (SEQ ID NO: 28) gggatgtttgctcca accaa |
| Asz1 | (SEQ ID NO: 29) gagtgggcttctccc agaaa | (SEQ ID NO: 30) ggtcattttcccgct cattc |
| Wdfc15a | (SEQ ID NO: 31) tgtgtggaaccctgg acaac | (SEQ ID NO: 32) gccaatgccgtcgtt atttt |
| Dazl | (SEQ ID NO: 33) caactgttaactacc actgcag | (SEQ ID NO: 34) caagagaccactgtc tgtatgc |
| Gapdh | (SEQ ID NO: 35) ttcaccaccatggag aaggc | (SEQ ID NO: 36) ccctttttggctccac cct |

Example 2

αKG Regulates Cellular Epigenetic Changes

Figure 3A:
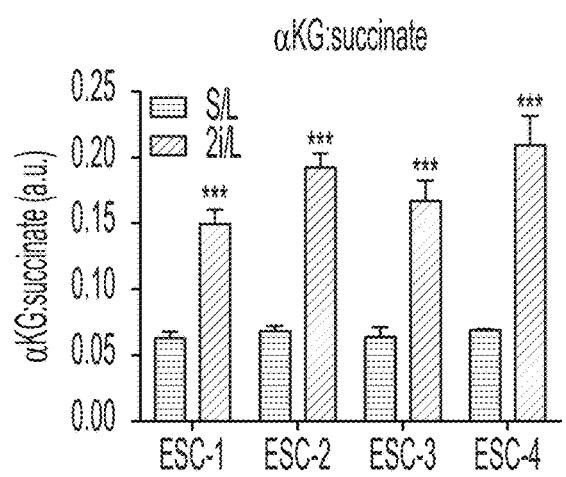

The greater utilization of glucose to support TCA cycle anaplerosis exhibited by cells grown in 2i/L medium suggested a potential explanation for the observed elevation in αKG despite reduced levels of TCA cycle intermediates. Diminished glutamine entry into the TCA cycle, coupled with the observed efflux of glucose-derived carbons from the TCA cycle as glutamate, suggested that cells cultured in 2i/L might not be oxidizing all the αKG produced from glutamine in the mitochondria. Indeed, the αKG:succinate ratio was robustly elevated by 2i/L in every ESC line tested (FIG. 3a). Cellular αKG:succinate ratios have been implicated in the regulation of the large family of αKG-dependent dioxygenases[15]. These enzymes utilize αKG as a co-substrate and produce succinate as an end product; succinate in turn can act as a competitive inhibitor of αKG-dependent dioxygenases. Consequently, the αKG:succinate ratio is an important driver of the equilibrium state of these enzymes. As Jumonji-domain containing histone demethylases and the Tet family of DNA demethylases comprise a major subset of these enzymes, the elevated ratio of αKG:succinate observed in cells grown in 2i/L medium could have important implications for the regulation of chromatin structure.

Figure 3B:
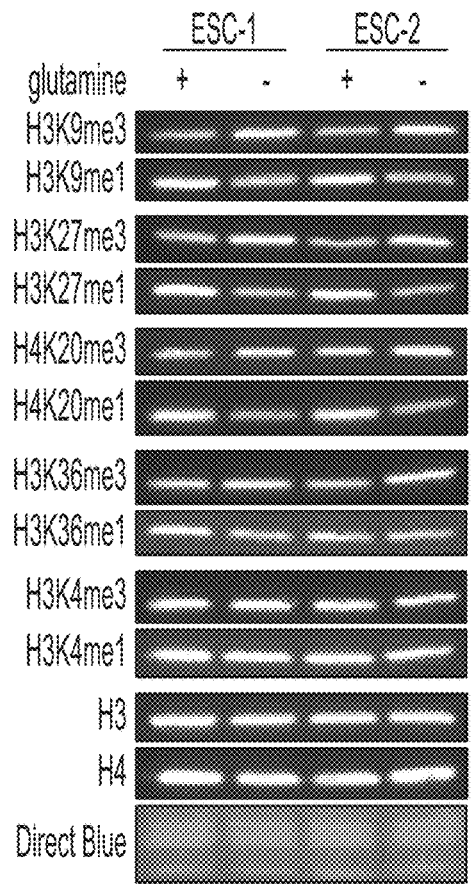
Figure 7A:
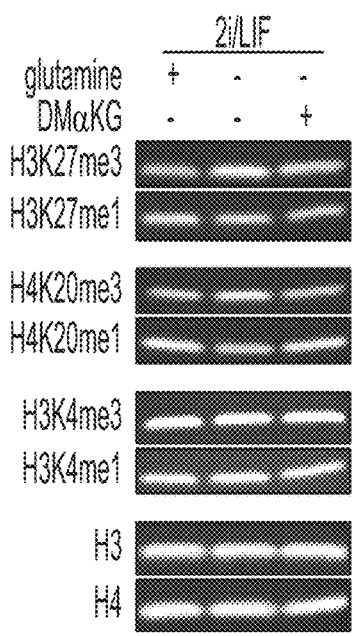
FIGS. 7A to 7C show FIG. 7A, Western blot of ESC-1 cells grown in glutamine-free S/L or 2i/L media for 24 hours with supplementation as indicated (DM-αKG, dimethyl-α-ketoglutarate).

Since αKG was largely derived from glutamine metabolism (FIG. 2d), the inventors tested whether glutamine deprivation affected histone lysine methylations known to be regulated in part by αKG-dependent demethylases[16]. ESCs growing in 2i/L were switched to glutamine-free 2i/L medium for three days and their histone methylation state examined. Cells transferred to glutamine-free medium exhibited increases in lysine tri-methylation and decreases in mono-methylation on H3K9, H3K27, H3K36, H4K20 while H3K4 methylations remained unchanged (FIG. 3b). To confirm that these changes could be accounted for by the decline in glutamine-dependent αKG, the inventors also demonstrated that DM-αKG addition reversed the increase in H3K27me3 and H4K20me3 observed in glutamine deficient medium (FIG. 7a).

Figure 3C:
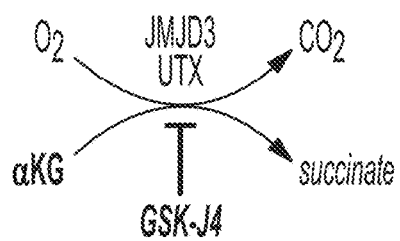
Figure 3D:
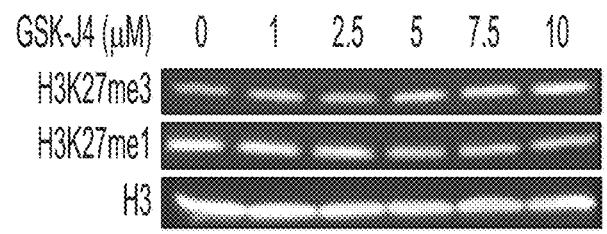

The above data suggest that the methylations of certain histone lysines, including H3K27, is being actively suppressed by αKG-dependent histone demethylases in cells maintained in 2i/L medium. To investigate this possibility, the inventors used a cell-permeable inhibitor GSK-J4[17] that preferentially inhibits UTX and Jmjd3, the two H3K27me3-specific KDM6 JmjC-family histone demethylases (FIG. 3c). Treatment with GSK-J4 induced a dose-dependent increase in H3K27me3 with a concomitant reduction of H3K27me1 that was comparable in magnitude to the difference observed when cells were cultured in the presence or absence of glutamine (FIG. 3b,d).

Figure 7B:
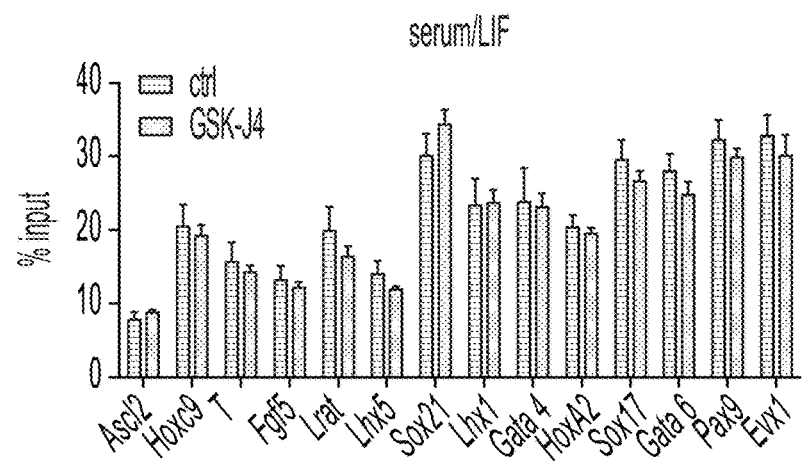
Figure 7C:

In ES cells "bivalent domains" are developmentally regulated genomic regions characterized by the co-localization of H3K4me3 and H3K27me3 and are thought to reflect a chromatin state primed for transition to either active or repressed chromatin during differentiation[18-20]. Recent genome-wide analysis of H3K4me3 and H3K27me3 in either S/L or 2i/L cultured ESCs reported that H3K27me3 was specifically depleted at bivalent domain gene promoters in 2i/L cultured cells.[10] The present data suggest that observed increases in αKG may promote αKG-dependent H3K27me3 demethylation in 2i/L ES cells. Conversely, the higher levels of H3K27me3 reported in S/L ESCs[10] may reflect a reduction in the αKG:succinate ratio that limits activity of histone demethylases. Consistent with this, the inventors found that the levels of H3K27me3 at bivalent domain promoters did not change when cells grown in S/L medium were treated with the H3K27me3 demethylase inhibitor GSK-J4 (FIG. 3e and FIG. 7b). In contrast, a similar treatment in 2i/LIF ESCs resulted in a consistent increase in H3K27me3 at bivalent domain promoters (FIG. 3e and FIG. 7c). The average fold-change across 14 bivalent promoters tested showed a highly significant increase in 2i/L-cultured ESCs compared to S/L-cultured ESCs (p<0.0001) (FIG. 3f). To confirm these findings genetically, the inventors generated two independent cell lines with mutations in the Jumonji domain of the H3K27me3 demethylase JMJD3 using CRISPR/Cas9 genome editing technologies (JMJD3ΔΔ/Δ-1 and JMJD3Δ/Δ-2) (FIG. 8a-c). Similar to treatment with GSK-J4, mutations in JMJD3 produced increases in H3K27me3 levels that were significantly higher in cells cultured in 2i/L, reflecting enhanced demethylation at these loci in mESCs cultured in 2i/L (FIG. 3f).

The present data indicate that 2i/L rewires glutamine metabolism to maintain αKG pools that favor active demethylation of a variety of histone marks. To test whether histone demethylation is a significant source of αKG consumption, cells were incubated with GSK-J4 or the inactive isomer GSK-J5 for 3 hours and αKG and succinate levels were monitored. Inhibition of UTX and JMJD3 triggered increases in the αKG:succinate ratio in cells cultured in both S/L and 2i/L. However, both the absolute and relative increase in the αKG:succinate ratio induced by GSK-J4 was more pronounced in the cells grown in 2i/L medium, whereas GSK-J5 had no effect (FIG. 3g). These data suggest that a significant amount of the αKG in cells grown in 2i/L is being consumed to maintain the demethylation of H3K27, while in S/L medium, H3K27 demethylation consumes less αKG.

In addition to reduced H3K27me3 at bivalent domain promoters, cells cultured in 2i/L exhibit DNA hypomethylation.[4,6-8] Previous work demonstrated that incubating cells with ascorbic acid, a cofactor for αKG-dependent dioxygenases, is sufficient to induce the activity of Tet enzymes and DNA demethylation in mESCs, resulting in enhanced expression of a panel of germline associated genes.[21] Therefore, the inventors tested whether αKG treatment could exert similar effects (FIG. 9b). Total DNA methylation was reduced in cells cultured with cell-permeable αKG (FIG. 9b). Alternatively or additionally, treatment with αKG, but not succinate, induced expression of ICM and germline-associated genes previously identified as targets of Tet-mediated activation (FIG. 9c).[21] The effects of αKG persisted upon extended passaging (FIG. 9d) and were largely abrogated in Tet1/Tet2 double knockout ES cells (FIG. 9e). These results suggest that intracellular αKG production may stimulate the activity of multiple αKG-dependent dioxygenases in order to coordinately regulate the epigenetic marks characteristic of naïve pluripotency.

Figure 4A:
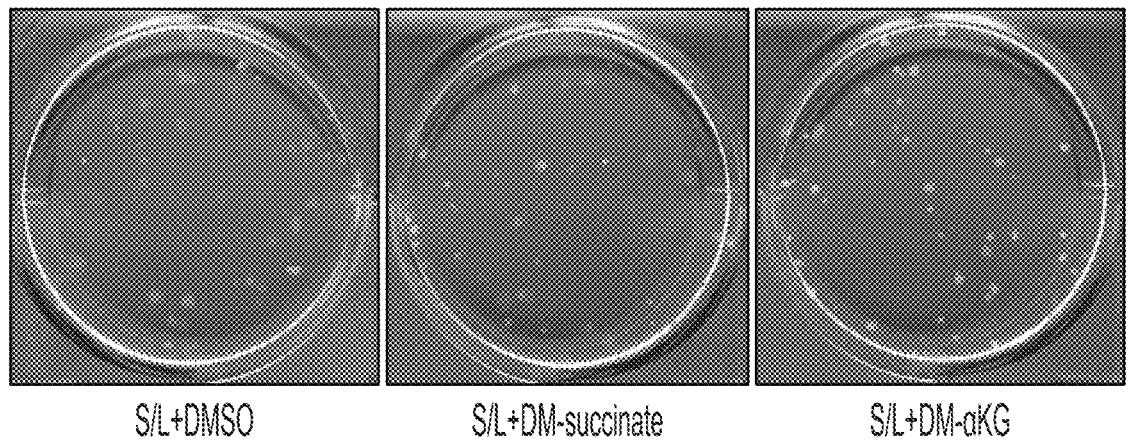
FIGS. 4A to 4C show FIG. 4A, Representative brightfield images of alkaline-phosphatase-stained colonies.
Figure 4B:
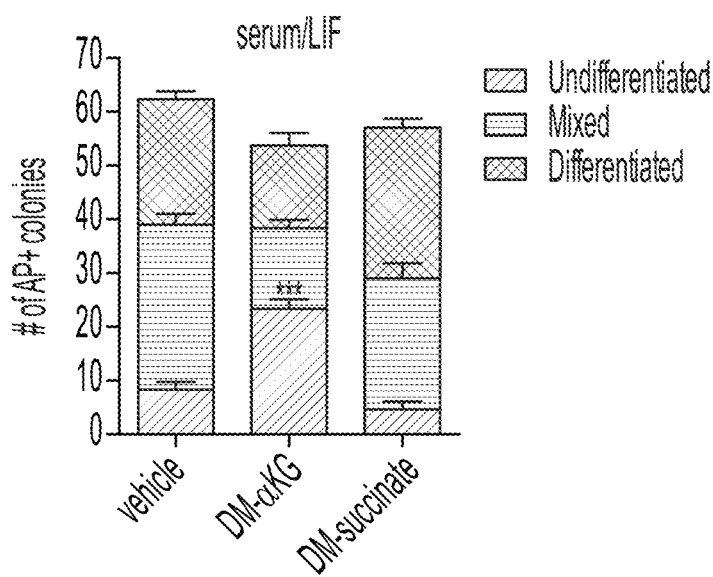
Figure 4C:
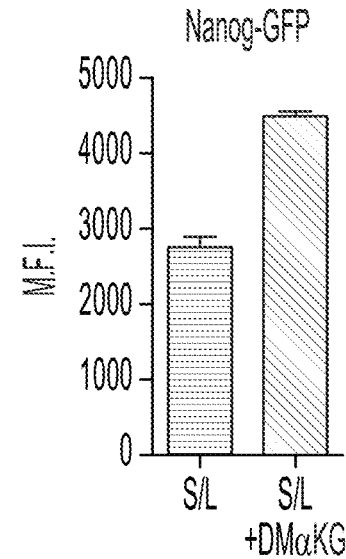
Figure 10A:
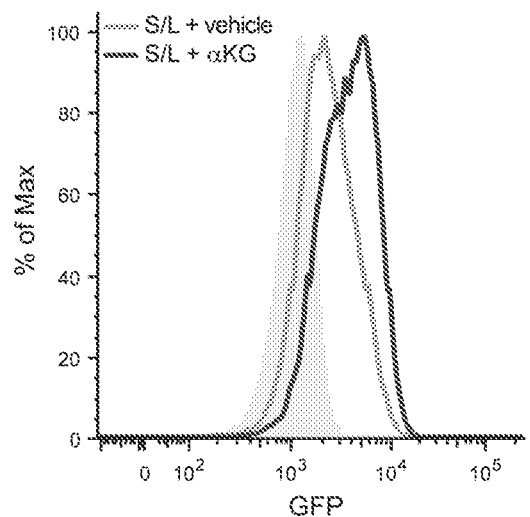
FIGS. 10A to 10B show FIG. 10A, Representative histogram of GFP intensity of Nanog-GFP cells treated with or without DM-αKG for three days.
Figure 10B:
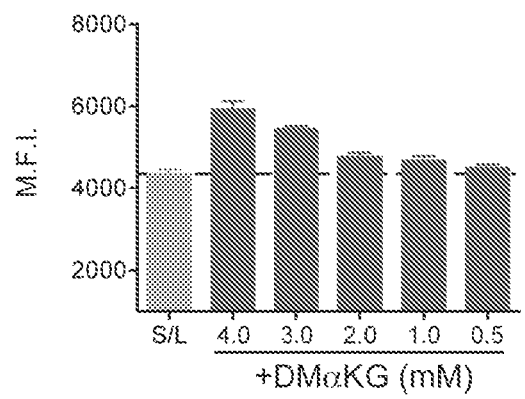

In ES cells, control of chromatin modifications through glutamine metabolism and αKG-dependent dioxygenases may not only regulate developmental genes but also help maintain the pluripotent state. To test whether modulation of the αKG:succinate ratio can influence pluripotent cell fate decisions, colony-forming assays were used to test whether manipulation of αKG and/or succinate could affect the self-renewal capacity of S/L ESCs. ESCs were plated at clonal density in S/L medium and the following day changed to S/L, SL+DM-succinate, or S/L+DM-αKG. After four days, colonies were stained with alkaline phosphatase and scored as differentiated, mixed or undifferentiated. Qualitative brightfield images showed that S/L+DM-αKG colonies stained brighter and retained a more compact colony morphology typical of undifferentiated ES cells (FIG. 4a). Indeed, while the total number of colonies were similar in all three conditions, the S/L+DM-αKG wells contained more than double the number of fully undifferentiated colonies compared to S/L and S/L+DM-succinate (p<0.0001), while the predominant colony types were either mixed or differentiated in both the S/L and S/L+DM-succinate treatments (FIG. 4b). Conversely, S/L+DM-succinate exhibited a reproducible trend of fewer undifferentiated and more differentiated colonies. As a further test of the ability of αKG to promote maintenance of ESCs, the inventors utilized a knock-in Nanog-GFP reporter line[22] and found that αKG was sufficient to enhance Nanog expression in a dose-dependent manner as detected by GFP fluorescence (FIG. 4c and FIG. 10). These results support the conclusion that αKG promotes the self-renewal of ES cells in vitro.

In conclusion, the above data demonstrate that the cellular ratio of αKG:succinate contributes to the ability of ES cells to suppress differentiation. The rewiring of cellular metabolism by inhibitors of GSK3β and MAPK/ERK signaling results in a reprogramming of glucose and glutamine metabolism that leads to accumulation of αKG and favors demethylation of repressive chromatin marks. The present results suggest that active αKG-dependent demethylation is a major regulatory mechanism governing the methylation state of repressive chromatin marks such as DNA methylation and H3K9me3, H3K27me3, and H4K20me3 in mESCs. Indeed recent clonal analysis of pluripotent cells revealed that DNA methylation is highly dynamic, balancing the antagonistic processes of removal and addition.[23] Further, in contrast to pluripotent ESCs, differentiated cells exhibit broad domains of H3K27me3 suggesting enhanced demethylase activity may also contribute to global reductions in H3K27me3 in pluripotent cells.[24,25] In contrast, the absence of an observed effect on activation-associated H3K4 methylation marks may reflect recent reports that H3K4me2/me3 is regulated in murine ESCs by threonine metabolism: threonine supports production of S-adenosylmethionine (SAM) to maintain a high SAM/SAH ratio critical to histone methyltransferase reactions.[26,27]

Supplementing mESC medium with ascorbic acid, a cofactor for αKG-dependent dioxygenase reactions, can also induce DNA demethylation and promote a blastocyst-like state in vitro.[21] Changes in other substrates, products, and/or cofactors of the large family of αKG-dependent dioxygenases may cooperate to influence chromatin state and cellular identity. While the inventors cannot rule out chromatin-independent effects of αKG supplementation on ESCs, our results support the notion that chromatin in pluripotent ESCs remains highly responsive to alterations in intracellular metabolism. Together, these results suggest that interconnections between signal transduction and cellular metabolism play a role in stem cell biology, organismal development and cellular differentiation.

Materials and Methods:

DNA methylation. Genomic DNA was extracted from ESC samples using Puregene Core Kit A (Sigma). DNA methylation was measured using the colorimetric Methyl-Flash Methylated DNA quantification kit (Epigentek) according to manufacturer instructions.

Chromatin immunoprecipitation. Native ChIP assays (histones) were performed with approximately 6×10⁶ ESCs per experiment. Cells were subject to hypotonic lysis and treated with micrococcal nuclease to recover mono- to tri-nucleosomes. Nuclei were lysed by brief sonication and dialyzed into N-ChIP buffer (10 mM Tris pH 7.6, 1 mM EDTA, 0.1% SDS, 0.1% Na-Deoxycholate, 1% Triton X-100) for 2 hr at 4° C. Soluble material was incubated overnight at 4° C. following addition of 3-5 µg of antibody bound to 75 µL protein A Dynal magnetic beads (Invitrogen), with 5% kept as input DNA. Magnetic beads were washed, chromatin was eluted, and ChIP DNA was dissolved in 10 mM Tris pH 8 for quantitative PCR reactions (see below).

ChIP-qPCR. Primers are listed below. All qPCR was performed using an Applied Biosystems StepOnePlus system and Power SYBR Green PCR master mix. ChIP samples were diluted 1:100 in H₂O and 5 µL used per reaction. ChIP-qPCR signals were calculated as percent input.

| Gene | Forward primer 5'→3' | Reverse primer 5'→3' |
|---|---|---|
| Gata6 | (SEQ ID NO: 37) cgcagcacacaggta cagtt | (SEQ ID NO: 38) gggatccaagcagat tgaaa |
| Pax9 | (SEQ ID NO: 39) aggtgtgcgacagct aaagg | (SEQ ID NO: 40) atcaacccggagtga tcaag |
| Lhx1 | (SEQ ID NO: 41) tgccaggcaccatta cagt | (SEQ ID NO: 42) aggcaaaggaaaaac catga |
| Hoxa2 | (SEQ ID NO: 43) ccaatgacaatttgg gcttt | (SEQ ID NO: 44) tgaggcgttcctttc tgact |
| Hoxc9 | (SEQ ID NO: 45) ttcttcccttttggcc ttttt | (SEQ ID NO: 46) agggtgtcttggctc tctca |
| Evx1 | (SEQ ID NO: 47) gccaggtgatctggg tgggga | (SEQ ID NO: 48) tgagaaccggccttg tgtct |
| Fgf5 | (SEQ ID NO: 49) gggatctcctgtgcc tggggt | (SEQ ID NO: 50) aggcctgtactgcag ccacattt |
| Ascl2 | (SEQ ID NO: 51) gctccagaagcagtt ctccctga | (SEQ ID NO: 52) gatagagccagagcc caagcccc |
| Lrat | (SEQ ID NO: 53) ccaagtccttcagtc tcttgcccc | (SEQ ID NO: 54) ggccacacaggctgc ttcca |
| Lhx5 | (SEQ ID NO: 55) aacccttaggcccca gcccc | (SEQ ID NO: 56) cgtgggcctggaggg gagaa |
| Sox17 | (SEQ ID NO: 57) gtctccccatgtagc tctcctgcc | (SEQ ID NO: 58) agaagagtcactgtg gaggtgaggg |
| Brachyury | (SEQ ID NO: 59) gccactgattcccga gaccc | (SEQ ID NO: 60) ccaggacaggcaggg tagggg |
| Gata4 | (SEQ ID NO: 61) acgtgtggtgttaat gtgcaagcc | (SEQ ID NO: 62) tgcccacaagcctgc gatcc |
| Sox21 | (SEQ ID NO: 63) aacagacatgccagt cagcagtgg | (SEQ ID NO: 64) ttagcatcgcaccac ccagagtc |
| Pou5f1 | (SEQ ID NO: 65) gaggtcaaggctaga gggtgg | (SEQ ID NO: 66) agggacggtttcacc tctcc |

CRISPR/Cas9 ESCs. A Cas9-2A-PURO plasmid was purchased from Addgene (Addgene plasmid 48139).[7] Two gRNAs targeting exon 17 of mouse JMJD3 were designed using the online software (crispr.mit.edu) resource from the Zhang Laboratory (MIT Cambridge, Mass. USA) and were cloned into Cas9-2A-Puro using the BbsI restriction enzyme sites. ESC-1 cells cultured in 2i/L medium were transfected with either Cas9-2A-Puro control or Jmjd3 gRNA-containing plasmids using Lipofectamine 2000 (Life Technologies). After 24 hours, cells were changed to fresh medium containing 1 µg/ml puromycin for 48 hours. Following selection, cells were cultured for 24 hours in 2i/L medium and then split to clonal density. After approximately 7 days, colonies were picked and expanded for analysis. Genomic DNA was purified from individual clones and used for PCR amplification of regions surrounding each gRNA target site. gRNA #1 product is 367 bp and gRNA #2 317 bp. Cloning of PCR products was performed using pGEM-T Easy (Promega). Mutants were identified by Sanger sequencing (Genewiz Inc.).

| gRNA oligos | Forward primer 5'→3' | Reverse primer 5'→3' |
|---|---|---|
| Jmjd3 gRNA #1 | (SEQ ID NO: 67) cacctgtggatgtta cccgcatga | (SEQ ID NO: 68) aaaactcatgcgggta acatccaca |
| Jmjd3 gRNA #2 | (SEQ ID NO: 69) caccgtccctggcag ccgaacgcc | (SEQ ID NO: 70) aaacggcgttcggct gccagggac |

| PCR primers | Forward primer 5'→3' | Reverse primer 5'→3' |
|---|---|---|
| Jmjd3 gRNA #1 | (SEQ ID NO: 71) ggctaaggcctaaga gtgcg | (SEQ ID NO: 72) cggacccaagaacc atcac |

-continued

| PCR primers | Forward primer 5'→3' | Reverse primer 5'→3' |
|---|---|---|
| Jmjd3 gRNA #2 | (SEQ ID NO: 73) tggcctgcagaggga gatag | (SEQ ID NO: 74) atttcgtcggcattc ctgtg |

FACS. Nanog-GFP ESCs[8] were cultured in S/L experimental medium for three passages and $2.5 \times 10^4$ cells were plated into a 6-well plate. Twenty-four hours later media was changed to S/L medium containing vehicle control or DM-AKG. Media was subsequently changed 48 hours later and cells harvested the following day. FACS analysis was performed at The Rockefeller University Flow Cytometry Resource Center using a BD LSR II. Data was generated using FlowJo. Analysis was performed on biological triplicates.

Antibodies. The following antibodies were used for Western blotting: H3 (Abcam 1791), H3K4me3 (Active Motif 39159), H3K4me1 (Millipore 07-436), H3K9me1 (kind gift of T. Jenuwein), H3K9me3 (Active Motif 39161), H4 (Abcam #0158), H4K20me1 (Abcam 9051), H4K20me3 (Millipore 07-463), H3K27me1 (Millipore 07-448), H3K27me3 (Millipore 07-449), H3K36me3 (Abcam 9050) and H3K36me1 (Millipore 07-548). The antibodies used for ChIP-qPCR were H3K27me3 (Cell Signaling 9733BF) and H3K4me3 (Active Motif 39159).

Self-renewal assays. ES cells free of feeder MEFs were plated at 100 cells per well in 6-well plates coated with 20 μg/mL mouse laminin (Stemgent 06-0002) in maintenance S/L medium. The following day media was changed to S/L experimental medium containing dimethyl-α-ketoglutarate (4 mM, Sigma 349631), dimethyl-succinate (4 mM, Sigma W239607) or DMSO vehicle control. Four days later cells were washed with PBS and stained for alkaline phosphatase using Vector Red Alkaline Phosphatase Kit (Vector Labs) according to manufacturer's instructions.

Statistics. Comparisons were made using unpaired two-tailed Student's t-tests or 2-way ANOVA with appropriate post-test (determined using GraphPad Prism) as indicated.

REFERENCES

1. Ying, Q. L. et al. The ground state of embryonic stem cell self-renewal. Nature 453, 519-23 (2008).
2. Gafni, O. et al. Derivation of novel human ground state naive pluripotent stem cells. Nature 504, 282-6 (2013).
3. Nichols, J., Silva, J., Roode, M. & Smith, A. Suppression of Erk signalling promotes ground state pluripotency in the mouse embryo. Development 136, 3215-22 (2009).
4. Smith, Z. D. et al. A unique regulatory phase of DNA methylation in the early mammalian embryo. Nature 484, 339-44 (2012).
5. Wray, J., Kalkan, T. & Smith, A. G. The ground state of pluripotency. Biochem Soc Trans 38, 1027-32 (2010).
6. Leitch, H. G. et al. Naive pluripotency is associated with global DNA hypomethylation. Nat Struct Mol Biol 20, 311-6 (2013).
7. Ficz, G. et al. FGF signaling inhibition in ESCs drives rapid genome-wide demethylation to the epigenetic ground state of pluripotency. Cell Stem Cell 13, 351-9 (2013).
8. Habibi, E. et al. Whole-genome bisulfite sequencing of two distinct interconvertible DNA methylomes of mouse embryonic stem cells. Cell Stem Cell 13, 360-9 (2013).
9. Borgel, J. et al. Targets and dynamics of promoter DNA methylation during early mouse development. Nat Genet 42, 1093-100 (2010).
10. Marks, H. et al. The transcriptional and epigenomic foundations of ground state pluripotency. Cell 149, 590-604 (2012).
11. Eagle, H., Oyama, V. I., Levy, M., Horton, C. L. & Fleischman, R. The growth response of mammalian cells in tissue culture to L-glutamine and L-glutamic acid. J Biol Chem 218, 607-16 (1956).
12. Ying, Q. L., Nichols, J., Chambers, I. & Smith, A. BMP induction of Id proteins suppresses differentiation and sustains embryonic stem cell self-renewal in collaboration with STAT3. Cell 115, 281-92 (2003).
13. Lunt, S. Y. & Vander Heiden, M. G. Aerobic glycolysis: meeting the metabolic requirements of cell proliferation. Annu Rev Cell Dev Biol 27, 441-64 (2011).
14. Zhang, J., Nuebel, E., Daley, G. Q., Koehler, C. M. & Teitell, M. A. Metabolic regulation in pluripotent stem cells during reprogramming and self-renewal. Cell Stem Cell 11, 589-95 (2012).
15. Kaelin, W. G., Jr. Cancer and altered metabolism: potential importance of hypoxia-inducible factor and 2-oxoglutarate-dependent dioxygenases. Cold Spring Harb Symp Quant Biol 76, 335-45 (2011).
16. Cloos, P. A., Christensen, J., Agger, K. & Helin, K. Erasing the methyl mark: histone demethylases at the center of cellular differentiation and disease. Genes Dev 22, 1115-40 (2008).
17. Kruidenier, L. et al. A selective jumonji H3K27 demethylase inhibitor modulates the proinflammatory macrophage response. Nature 488, 404-8 (2012).
18. Bernstein, B. E. et al. A bivalent chromatin structure marks key developmental genes in embryonic stem cells. Cell 125, 315-26 (2006).
19. Boyer, L. A. et al. Polycomb complexes repress developmental regulators in murine embryonic stem cells. Nature 441, 349-53 (2006).
20. Mikkelsen, T. S. et al. Genome-wide maps of chromatin state in pluripotent and lineage-committed cells. Nature 448, 553-60 (2007).
21. Blaschke, K. et al. Vitamin C induces Tet-dependent DNA demethylation and a blastocyst-like state in ES cells. Nature 500, 222-6 (2013).
22. Faddah, D. A. et al. Single-cell analysis reveals that expression of nanog is biallelic and equally variable as that of other pluripotency factors in mouse ESCs. Cell Stem Cell 13, 23-9 (2013).
23. Shipony, Z. et al. Dynamic and static maintenance of epigenetic memory in pluripotent and somatic cells. Nature 513, 115-9 (2014).
24. Zhu, J. et al. Genome-wide chromatin state transitions associated with developmental and environmental cues. Cell 152, 642-54 (2013).
25. Hawkins, R. D. et al. Distinct epigenomic landscapes of pluripotent and lineage-committed human cells. Cell Stem Cell 6, 479-91 (2010).
26. Wang, J. et al. Dependence of mouse embryonic stem cells on threonine catabolism. Science 325, 435-9 (2009).
27. Shyh-Chang, N. et al. Influence of threonine metabolism on S-adenosylmethionine and histone methylation. Science 339, 222-6 (2013).

What is claimed is:

1. A method for enriching a population of cells for human or mouse pluripotent stem cells, the method comprising steps of:
   a) providing a population of cells comprising a mixture of pluripotent stem cells and non-pluripotent cells, wherein the pluripotent stem cells are human or mouse pluripotent stem cells; and
   b) culturing the population of cells comprising the mixture of pluripotent stem cells and non-pluripotent cells in a culture medium substantially free of glutamine, wherein the culture medium comprises 0.5 mM-4 mM of cell-permeable dimethyl-α-ketoglutarate (αKG), a mitogen activated protein kinase (MAPK) inhibitor and/or a glycogen synthase kinase 3β (GSKβ) inhibitor;
   wherein the pluripotent stem cells have a higher proliferation rate and/or survival rate compared to the non-pluripotent cells during said culturing, thereby producing a population in which pluripotent stem cells are enriched relative to non-pluripotent cells as compared to the provided population of cells.

2. The method of claim 1, wherein the medium comprises the mitogen activated protein kinase (MAPK) inhibitor and the glycogen synthase kinase 3β (GSK3β) inhibitor.

3. The method of claim 1, wherein the pluripotent stem cells are embryonic stem cells.

4. The method of claim 1, wherein the pluripotent stem cells are induced pluripotent stem cells.

5. The method of claim 1, wherein the provided population of cells comprises an ex vivo population of cells.

6. The method of claim 1, wherein the produced population comprises at least 60% human or mouse pluripotent stem cells.

* * * * *

UNITED STATES PATENT AND TRADEMARK OFFICE
CERTIFICATE OF CORRECTION

PATENT NO. : 11,203,739 B2
APPLICATION NO. : 15/302560
DATED : December 21, 2021
INVENTOR(S) : Lydia W. S. Finley et al.

It is certified that error appears in the above-identified patent and that said Letters Patent is hereby corrected as shown below:

In the Specification

At Column 1, Line 16, please replace the paragraph and insert the following new paragraph:
--GOVERNMENT SUPPORT
This invention was made with government support under CA105463 awarded by the National Institutes of Health. The government has certain rights in the invention.--

Signed and Sealed this
Twelfth Day of March, 2024

Katherine Kelly Vidal
*Director of the United States Patent and Trademark Office*

SEQUENCE LISTING

<160> NUMBER OF SEQ ID NOS: 74

<210> SEQ ID NO 1
<211> LENGTH: 31
<212> TYPE: DNA
<213> ORGANISM: Mus sp.

<400> SEQUENCE: 1
tgcctgtgga tgttacccgc atgaaggcgg g                          31

<210> SEQ ID NO 2
<211> LENGTH: 31
<212> TYPE: DNA
<213> ORGANISM: Mus sp.

<400> SEQUENCE: 2
cccgcctaca tgcgggtaac atccacaggc a                          31

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgtggatgtt acccgcatga                                       20

<210> SEQ ID NO 4
<211> LENGTH: 31
<212> TYPE: DNA
<213> ORGANISM: Mus sp.

<400> SEQUENCE: 4
gaaggtccct ggcagccgaa cgccaggtgt g                          31

<210> SEQ ID NO 5
<211> LENGTH: 31
<212> TYPE: DNA
<213> ORGANISM: Mus sp.

<400> SEQUENCE: 5
cacacctggc gttcggctgc cagggacctt c                          31

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtccctggca gccgaacgcc                                       20

<210> SEQ ID NO 7
<211> LENGTH: 23
<212> TYPE: DNA
<213> ORGANISM: Mus sp.

<400> SEQUENCE: 7
tgtggatgtt acccgcatga agg                                   23

```
<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgtggatgtt acccgtgaag g                                              21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgtggatgtt acccgaagg                                                 19

<210> SEQ ID NO 10
<211> LENGTH: 23
<212> TYPE: DNA
<213> ORGANISM: Mus sp.

<400> SEQUENCE: 10
gtccctggca gccgaacgcc agg                                            23

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtccctggca gccgaacagc cagg                                           24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtccctggca gccgaaccgc cagg                                           24

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acatcgccaa tcagcttgg                                                 19

<210> SEQ ID NO 14
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 14
agaaccatac tcgaaccaca tcc                                              23

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aagatgcgga ctgtgttctc                                                  20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgcttgcact tcatcctttg                                                  20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tttctggaac ccatggagag                                                  20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agccagcacc tccttctaca                                                  20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
taaaggcgca tctgcgtaca                                                  20

<210> SEQ ID NO 20
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 20
cgcacaagtg gcactgaaag                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tccaggccat caagagtttc                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atctgctggg ttctccactg                                                    20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaactccatg caagtgccaa at                                                 22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tctcggcctg tcttttcagt tc                                                 22

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgagtggcag tttcttcttg g                                                  21

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 26
cttcttgaac aatgcctatg actcacttcc                                        30

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tggcgctttt gactcaggat                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gggatgtttg ctccaaccaa                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gagtgggctt ctcccagaaa                                                   20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggtcattttc ccgctcattc                                                   20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgtgtggaac cctggacaac                                                   20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gccaatgccg tcgttatttt                                              20

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caactgttaa ctaccactgc ag                                           22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
caagagacca ctgtctgtat gc                                           22

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttcaccacca tggagaaggc                                              20

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cccttttggc tccaccct                                                18

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cgcagcacac aggtacagtt                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 38
gggatccaag cagattgaaa                                               20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aggtgtgcga cagctaaagg                                               20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
atcaacccgg agtgatcaag                                               20

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tgccaggcac cattacagt                                                19

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aggcaaagga aaaaccatga                                               20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ccaatgacaa tttgggcttt                                               20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
```
tgaggcgttc ctttctgact                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttcttccctt tggccttttt                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agggtgtctt ggctctctca                                              20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gccaggtgat ctgggtgggg a                                            21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tgagaaccgg ccttgtgtgc t                                            21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gggatctcct gtgcctgggg t                                            21

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aggcctgtac tgcagccaca ttt                                          23

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gctccagaag cagttctccc ctga                                         24

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gatagagcca gagcccaagc ccc                                          23

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ccaagtcctt cagtctcttg cccc                                         24

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggccacacag gctgcttcca                                              20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aacccttagg ccccagcccc                                              20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cgtgggcctg gaggggagaa                                              20

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gtctccccat gtagctctcc tgcc                                              24

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
agaagagtca ctgtggaggt gaggg                                             25

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gccactgctt tcccgagacc c                                                 21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ccaggacagg cagggtaggg g                                                 21

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
acgtgtggtg ttaatgtgca agcc                                              24

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tgcccacaag cctgcgatcc                                                   20

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aacagacatg ccagtcagca gtgg                                          24

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ttagcatcgc accacccaga gtc                                           23

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gaggtcaagg ctagagggtg g                                             21

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
agggacggtt tcacctctcc                                               20

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cacctgtgga tgttacccgc atga                                          24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
aaactcatgc gggtaacatc caca                                          24

```
<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
caccgtccct ggcagccgaa cgcc                                            24

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aaacggcgtt cggctgccag ggac                                            24

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggctaaggcc taagagtgcg                                                 20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cggaccccaa gaaccatcac                                                 20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tggcctgcag agggagatag                                                 20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
atttcgtcgg cattcctgtg                                                 20
```